United States Patent
Hadash

(10) Patent No.: US 10,046,123 B2
(45) Date of Patent: Aug. 14, 2018

(54) SYSTEMS AND METHODS FOR ADMINISTERING PULMONARY MEDICATIONS

(71) Applicant: INHALETECH LLC, Minneapolis, MN (US)

(72) Inventor: Joseph Hadash, Lapid (IL)

(73) Assignee: INHALETECH LLC, Minneapolis, MN (US)

( * ) Notice: Subject to any disclaimer, the term of this patent is extended or adjusted under 35 U.S.C. 154(b) by 286 days.

(21) Appl. No.: 14/439,625

(22) PCT Filed: Oct. 30, 2013

(86) PCT No.: PCT/IB2013/059799
§ 371 (c)(1),
(2) Date: Apr. 29, 2015

(87) PCT Pub. No.: WO2014/068504
PCT Pub. Date: May 8, 2014

(65) Prior Publication Data
US 2015/0273165 A1    Oct. 1, 2015

Related U.S. Application Data

(60) Provisional application No. 61/793,986, filed on Mar. 15, 2013, provisional application No. 61/795,930, filed on Oct. 31, 2012.

(51) Int. Cl.
*A61M 15/00*    (2006.01)
*A61M 16/08*    (2006.01)
(Continued)

(52) U.S. Cl.
CPC ........ *A61M 15/002* (2014.02); *A61M 15/009* (2013.01); *A61M 15/0021* (2014.02);
(Continued)

(58) Field of Classification Search
None
See application file for complete search history.

(56) References Cited

U.S. PATENT DOCUMENTS

| 5,027,808 A | 7/1991 | Rich et al. |
| 5,347,998 A | 9/1994 | Hodson et al. |
| (Continued) | | |

FOREIGN PATENT DOCUMENTS

| EP | 0232235 A2 | 8/1987 |
| EP | 2068983 A1 | 6/2009 |
| (Continued) | | |

OTHER PUBLICATIONS

International Preliminary Report on Patentability from International Application No. PCT/IB2013/059799, dated May 14, 2015, 11 pp.
(Continued)

*Primary Examiner* — Rachel T Sippel
(74) *Attorney, Agent, or Firm* — Roach Brown McCarthy & Gruber, P.C.; Kevin D. McCarthy

(57) ABSTRACT

Example techniques and systems include detecting patient inhalation with a pulmonary medication dosing device and controlling a valve to release medication based on the detection. For example, a method includes generating a signal indicative of air flow within a portion of a pulmonary medication dosing device, receiving, by a processor, a command based on the signal and associated with a valve configured to at least partially control release of medication via the pulmonary medication dosing device, and controlling, by the processor and based on the received command, the valve to release at least a portion of a dose of the medication into the air flow. In some examples, a mobile computing device may be configured to generate and transmit the command to the pulmonary medication dosing device for controlling the valve.

20 Claims, 13 Drawing Sheets

(51) Int. Cl.
*G06F 19/00* (2018.01)
*A61M 16/20* (2006.01)
*A61M 16/14* (2006.01)
*A61M 16/00* (2006.01)

(52) U.S. Cl.
CPC ........ *A61M 15/0065* (2013.01); *A61M 16/14* (2013.01); *A61M 16/202* (2014.02); *G06F 19/3462* (2013.01); *A61M 16/0833* (2014.02); *A61M 2016/0021* (2013.01); *A61M 2016/0033* (2013.01); *A61M 2205/3303* (2013.01); *A61M 2205/3306* (2013.01); *A61M 2205/3317* (2013.01); *A61M 2205/3334* (2013.01); *A61M 2205/3375* (2013.01); *A61M 2205/3553* (2013.01); *A61M 2205/3561* (2013.01); *A61M 2205/3569* (2013.01); *A61M 2205/3576* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/8206* (2013.01); *A61M 2205/8212* (2013.01); *A61M 2230/40* (2013.01)

(56) References Cited

U.S. PATENT DOCUMENTS

| | | | |
|---|---|---|---|
| 5,364,838 A | | 11/1994 | Rubsamen |
| 5,404,871 A | * | 4/1995 | Goodman ............ A61M 15/00 128/200.14 |
| 5,497,764 A | * | 3/1996 | Ritson ................ A61M 15/00 128/200.14 |
| 5,848,588 A | | 12/1998 | Foley et al. |
| 6,039,042 A | | 3/2000 | Sladek |
| 6,460,537 B1 | | 10/2002 | Bryant et al. |
| 6,637,432 B2 | | 10/2003 | Wakefield et al. |
| 6,672,304 B1 | | 1/2004 | Casper et al. |
| 6,810,872 B1 | * | 11/2004 | Ohki ................. A61M 15/0045 128/203.15 |
| 6,981,499 B2 | | 1/2006 | Anderson et al. |
| 7,841,337 B2 | | 11/2010 | Djupesland |
| 2006/0252998 A1 | | 11/2006 | Kimbrell |
| 2008/0246629 A1 | | 10/2008 | Tsui et al. |
| 2009/0156952 A1 | * | 6/2009 | Hunter ................ A61M 16/209 600/538 |
| 2009/0194104 A1 | | 8/2009 | Van Sickle |
| 2010/0071688 A1 | | 3/2010 | Dwyer |
| 2010/0114367 A1 | | 5/2010 | Barrett et al. |
| 2010/0192948 A1 | | 8/2010 | Sutherland et al. |
| 2010/0286488 A1 | | 11/2010 | Cohen et al. |
| 2010/0292556 A1 | | 11/2010 | Golden |
| 2011/0004888 A1 | | 1/2011 | Srinivasan et al. |
| 2011/0047135 A1 | | 2/2011 | Vizethann et al. |
| 2011/0161100 A1 | | 6/2011 | Peak et al. |
| 2011/0191767 A1 | | 8/2011 | Pinsky et al. |

FOREIGN PATENT DOCUMENTS

| | | |
|---|---|---|
| KR | 1020090094111 A | 9/2009 |
| WO | 0105458 A1 | 1/2001 |
| WO | 0245783 A1 | 6/2002 |
| WO | 2007041669 A2 | 4/2007 |
| WO | 2010070496 A1 | 6/2010 |

OTHER PUBLICATIONS

International Search Report and Written Opinion of International Application No. PCT/IB2013/059799, dated Sep. 23, 2014, 16 pp.
Invitation to Pay Additional Fees from International Application No. PCT/IB2013/059799, dated Feb. 18, 2014, 6 pp.
Invitation to Pay Additional Fees from International Application No. PCT/IB2013/059799, dated Jun. 30, 2014, 6 pp.
Communication pursuant to Article 94(3) EPC from counterpart European Patent Application 13802714.9, dated Dec. 7, 2017, 4 pp.
Communication pursuant to Article 94(3) EPC from counterpart European Application No. 13802714.9, dated Mar. 22, 2017, 4 pp.
Communication to Article 94(3) EPC dated Mar. 22, 2017 from counterpart European Patent Application No. 13802714.9, filed on Sep. 29, 2017, 15 pp.

* cited by examiner

SYSTEMS AND METHODS FOR ADMINISTERING PULMONARY MEDICATIONS

This application is a national stage entry under 35 U.S.C. § 371 of International Application No. PCT/IB2013/059799 filed Oct. 30, 2013, which claims the benefit of U.S. Provisional Application Nos. 61/793,986, filed Mar. 15, 2013, and 61/795,930, filed Oct. 31, 2012; the entire content of each of which being incorporated herein by reference.

TECHNICAL FIELD

The invention relates to medical devices and, more particularly, to the delivery of pulmonary medications by medical devices.

BACKGROUND

Various diseases and disorders may be treatable with pulmonary medication or any other inhaled substances. For example, obstructive lung disease may cause narrowing of the airways that result in obstructions and a reduction in the volume of air obtained by the patient. In some cases, this narrowing may be the result of a variety of causes such as inflammation of airway walls, contraction of smooth muscle surrounding the airways, and/or excess mucus inside an airway. Relieving this obstruction may enable easier breathing for the patient and a greater volume of fresh air that reaches the alveoli (i.e., air sacs) of the lungs.

For conditions such as these, a patient may benefit from emergency and/or maintenance respiratory therapy through delivery of drug to the airway. This drug delivery and management of pulmonary condition, such as obstructive airway disease, may be achieved through the use of an inhaler device. An inhaler device may be referred to as a metered dose inhaler in some examples. A patient may operate the inhaler device by placing the mouthpiece of the device inside the patient's mouth and inhaling while depressing a canister containing pressurized medication. Depression of the canister opens a metered valve of the canister such that the medication is released into the air flow of the inhalation of the patient.

SUMMARY

Generally, this disclosure describes various techniques and systems for controlling the release of a substance into an inhaled stream of air from a patient. For example, a pulmonary medication dosing device (PMDD) may be configured to trigger the release of at least a portion of a dose of medication in response to detection of air flow indicative of an inhalation by a patient. The PMDD may include a sensor that generates a signal indicative of the air flow through a portion of the PMDD (e.g., a housing and/or mouthpiece of the PMDD) caused by an inhaling action of the patient. In response to a command based on the signal indicative of the air flow, the PMDD may control a valve to open and release at least a portion of a dose of medication stored in a canister coupled to the PMDD.

In some examples, the PMDD may include processors and/or modules to generate the command such that the PMDD is configured to operate individually. In other examples, a computing device (e.g., a mobile computing device such as a smartphone, tablet computer, notebook computer, or portable medical device) may generate the command for controlling the valve to release the medication. The PMDD may transmit the signal indicative of the air flow to the computing device, the computing device may generate the command for controlling the valve, and the computing device may subsequently transmit the command to the PMDD for controlling the delivery of the medication from a canister coupled to the PMDD. By offloading at least some of the processing functions to the computing device, the PMDD may benefit from additional functionality of the computing device and be manufactured at a reduced cost, for example.

In one example, the disclosure describes a method that includes generating a signal indicative of air flow within a portion of a pulmonary medication dosing device, receiving, by a processor, a command based on the signal and associated with a valve configured to at least partially control release of a medication via the pulmonary medication dosing device, and controlling, by the processor and based on the received command, the valve to release at least a portion of a dose of the medication into the air flow.

In another example, the disclosure describes a pulmonary medication dosing device including a valve configured to at least partially control release of medication, a sensor configured to generate a signal indicative of air flow within a portion of the device, and a processor configured to receive a command based on the signal and associated with the valve and control, based on the received command, the valve to release at least a portion of a dose of the medication into the air flow.

In another example, the disclosure describes a system including a housing configured to accept a medication canister containing a medication, a dispensing portion coupled to the housing, a valve configured to at least partially control release of medication from the medication canister, a sensor configured to generate a signal indicative of air flow within the dispensing portion, and a processor configured to receive a command based on the signal and associated with the valve, and control, based on the received command, the valve to release at least a portion of a dose of the medication into the air flow within the dispensing portion.

In another example, the disclosure describes a computer-readable storage medium comprising instructions that, when executed by one or more processors of a computing device, cause the one or more processors to receive data indicative of air flow within a portion of a pulmonary medication dosing device, responsive to receiving the data, generate, based on the received data, a command associated with a valve configured to at least partially control release of a medication via the pulmonary medication dosing device, and wherein the command indicates one of an open configuration or a closed configuration of the valve, and transmit the command to a communication unit associated with the pulmonary medication dosing device.

DETAILED DESCRIPTION

Figure 1:
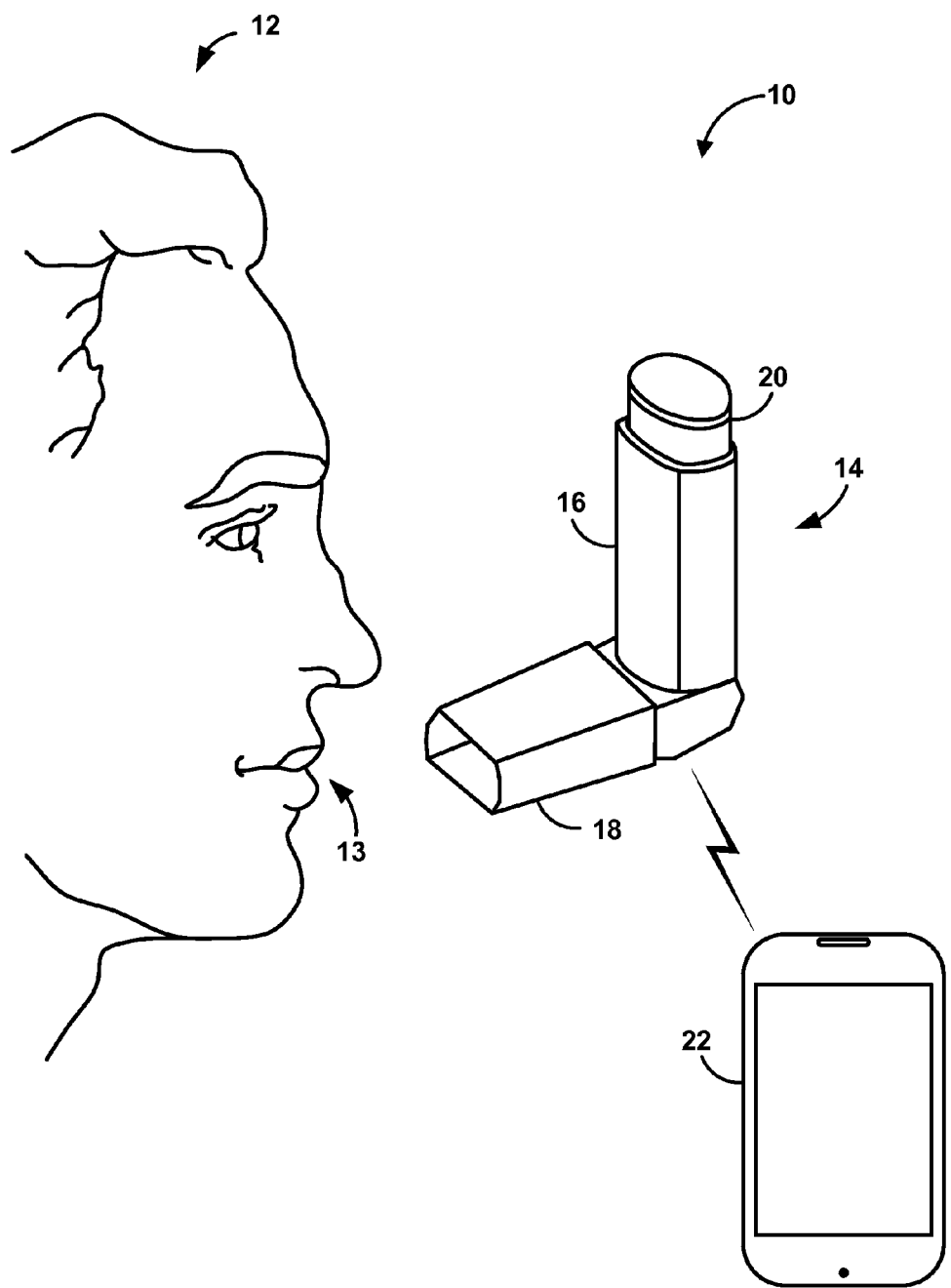
FIG. 1 is a conceptual drawing illustrating an example system that includes a pulmonary medication delivery device (PMDD) and a computing device in relation to a user.

This disclosure describes various techniques and systems for controlling the release of a substance into an inhaled stream of air from a patient. Typically, patients requiring pulmonary medications to treat various disorders and conditions may rely upon metered dose inhalers (MDIs) or other delivery devices to obtain the prescribed pulmonary medication. To receive medication from an example MDI, a patient attempts to coordinate an inhaled breath with the manual depression of a medication canister coupled to a housing of the MDI.

Efficacy of medication delivery using an MDI may depend on a variety of factors, such as the ability of the patient to accurately coordinate breathing and hand manipulation functions, effective mixture of the medication with turbulent airflows associated with the use of inhaling devices, and a sufficient volume of inhaled air to deposit the medication within the air ways (bronchi and bronchioles) and air sacs (alveoli). Even if the patient uses an optimal technique for delivering the medication, only 15-30% percent of the dispensed medication may be deposited within the lungs of the patient. Under these conditions, it can be difficult to determine appropriate dosing of medication for specific patients, and patients may not receive a sufficient amount of medication as a result of changing conditions and inconsistent delivery technique. A "spacer" or "space cell" may be added to an MDI in an attempt to improve the delivery of medication from the MDI to the lungs. The spacer may be a long cylinder added to the mouthpiece of the MDI, and medication is delivered into the spacer such that the patient inhales the medication present within the spacer. However, spacers have a relatively large physical size, are expensive, and may result in medication deposited on a wall of the spacer instead of delivered to the lungs of the patient.

As described herein, various devices and systems may function to deliver pulmonary medication to a patient in response to detecting patient inhalations, as opposed to relying upon patient coordination of inhalation and manual manipulation of an MDI. For example, a pulmonary medication dosing device (PMDD) may be configured to trigger the release of at least a portion of a dose of medication in response to detection of air flow indicative of an inhalation by a patient. The PMDD may include a sensor that generates a signal indicative of the air flow (e.g., pressure and/or fluid flow) through a portion of the PMDD (e.g., a housing and/or mouthpiece of the PMDD). The patient causes the air flow by placing a portion of the PMDD into the mouth and inhaling a volume of air. In response to a command based on the generated signal indicative of the air flow, the PMDD may control a valve to open and release at least a portion of a dose of medication stored in a canister coupled to the PMDD. The PMDD may be configured to accept canisters already used with typical MDIs. A PMDD as described herein may improve the efficacy of traditional pulmonary medication delivery devices (e.g., MDIs). A PMDD may also be described as a "virtual spacer" that may provide some advantages of a spacer for an MDI at a reduced size, reduced price, and without the potential deposition of medication on the walls of a traditional spacer.

In some examples, the PMDD may include processors and/or modules to generate the command such that the PMDD is configured to operate individually. For example, the PMDD may receive the generated signal from an air flow sensor, determine a parameter value representative of the signal, and generate the command based on the parameter value. The PMDD may generate a command to open the valve and release medication in response to the parameter value exceeding a threshold indicative of an inhalation event. In addition, the PMDD may generate a command to close the valve in response to detecting the parameter value below the threshold, a cumulative volume of air exceeding a threshold, or determining a time period has elapsed, for example. The determined parameter value may be representative of an air flow rate (e.g., cubic meters per second), an air flow velocity, or a pressure of the air flow.

In other examples, a computing device (e.g., a mobile computing device such as a smartphone, tablet computer, notebook computer, or portable medical device) may generate the command for controlling the valve of the PMDD to release the medication. In response to generating the signal indicative of the air flow, the PMDD may transmit the signal to the computing device, the computing device may analyze the signal and generate the command for controlling the valve, and the computing device may subsequently transmit the command to the PMDD for controlling the delivery of the medication from canister coupled to the PMDD. By offloading at least some of the processing functions to the computing device, the PMDD may benefit from additional functionality (e.g., greater processing power, greater memory for storing instructions relating to generating a command to control the valve of the PMDD, access to networked devices, etc.) of the computing device and be manufactured at a reduced cost, for example.

In some examples, the PMDD sensor may include a spindle or other rotating device, a vane, or pressure sensor configured to convert a mechanical deformation due to the air flow to an electrical signal indicative of the air flow. In this manner, a magnitude and/or direction of air flow within the PMDD or indicative of patient breath may be detected by sensing flow of fluid or gas and/or changes in pressure at one or more locations. In other examples, the computing device may detect the generated signal indicative of air flow using an optical sensor (e.g., a camera), a magnetic field sensor, or any other sensor configured to detect a change in the PMDD sensor due to air flow. For example, the PMDD sensor may be a spindle or vane placed within the path of the air flow such that movement of the sensor is visually detectable through a transparent portion of the PMDD by the optical sensor of the computing device. The valve of the PMDD may be an electro-mechanical valve configured to open and/or close in response to an electrical signal. In some examples, the PMDD may control the valve to deliver a single sub-dose of medication for each inhalation. In this manner, the valve may allow the PMDD and/or computing device to segment a full dose of medication into a plurality of smaller sub-doses more appropriate for the flow rate, velocity, and/or volume of air actually inhaled by the patient.

Although the PMDD may be described as generally including components to provide the functionality described herein, the PMDD may include a housing typical for MDIs and an add-on device that includes a valve, sensor, and other electronics necessary to perform the functions described herein. The add-on may take the form of a mouthpiece configured to be coupled to an MDI housing that accepts a medication canister. In this manner, the add-on portion of the PMDD may be an additional device that the patient may add to a previously used MDI.

Although this disclosure is generally described with respect to pulmonary medications, the techniques and devices described herein may be used for delivery of any substance in response to detecting an air flow. For example, a patient may use a PMDD to receive medication directed to the mouth, throat, nasal passages, etc.

FIG. 1 is a conceptual drawing illustrating an example system 10 that includes pulmonary medication delivery device (PMDD) 14 and computing device 22 in relation to user 12. PMDD 14 may include a mouthpiece 18 and housing 16. Mouthpiece 18 may be removably attached to housing 16, permanently coupled to housing 16, or formed with housing 16, for example. Housing 16 may be configured to accept canister 20, wherein canister 20 includes a medication to be dispensed to patient 12 via PMDD 14. Canister 20 may be replaceable or exchangeable such that PMDD 14 can accept a variety of different canisters containing any number of different medications. A large patient population may benefit from respiratory therapy, either maintenance therapy or emergency therapy, through the delivery of medication to airways through the use of inhaler devices.

PMDD 14 and system 10 may be used to achieve improved delivery of pulmonary medication (or any other airborne substance) to patient 12. The respiratory tract can be considered as a filter that removes particles from inspired air. The effectiveness of this filter depends on particle properties (e.g. size, shape, density, and charge), respiratory tract morphology, and the breathing pattern (e.g. airflow rate and tidal volume) of patient 12. These various factors may determine the quantity of particles that are deposited in the respiratory tract and in what region of the respiratory tract the particles are deposited. For example, the density of an inhaled gas may influence deposition of aerosol substances in the lung. Moreover, high inspiratory airflows often employed by patient 12 during use of inhaling devices (e.g., MDIs or nebulizers). These high air flows are typically associated with higher turbulence, but inhalation of a less dense gas can contribute to less turbulent, and more laminar, airflow within the respiratory tract.

To achieve an adequate therapeutic effect from inhaled medication, a sufficient deposition of medication must be made in the medium and small airways of patient 12. This desired result may require a competent inhalation technique if the delivery device is patient-activated, irrespective of the design and relative complexity of any specific manual inhalation device. However, even an optimal inhalation technique may result in only a small portion of the medication dose from even reaching the target tissues within the lungs. This problem is made worse with the use of inadequacies of user technique, such as coordination between breathing and manipulation of the MDI. Although typical MDIs may be relatively inexpensive and easy to carry by a patient, they may not provide efficacious treatment in all cases or at all times. System 10 may be directed to addressing some of these issues, such as improving the amount of medication reaching the lungs of patient 12 by automating the release of medication in response to detection of a patient-initiated breath, or inhalation.

Patient 12 may use PMDD 14 to deliver a dose of medication from canister 20 into the lungs of patient 12. Patient 12 may place a portion of mouthpiece 18 into mouth 13. In some examples, mouthpiece 18 may be referred to a dispensing portion of PMDD 14, and mouthpiece 18 may include or define a nozzle within which air flows into patient 12. With canister 20 depressed such that a metered valve of canister 20 is open, patient 12 may begin to inhale air through an interior channel formed by mouthpiece 18. In response to this inhalation, a sensor (not shown) within PMDD 14 may generate a signal indicative of the air flow of the inhalation toward patient 12. Based on the generated signal, a processor of PMDD 14 and/or computing device 22 may generate a command such that PMDD 14 can control the valve (not shown) to open and release medication from canister 20. The generated command, or a second command, may indicate when PMDD 14 is to control the valve to close.

Canister 20 may include a metering valve that controls the release of medication from canister 20. The metering valve may include a spring or other mechanism that configures the metering valve in a closed state without any external forces acting on the metering valve. In response to depressing the metering valve (e.g., compressing the spring of the metering valve) the metering valve may open to release a predetermined dose of the medication. When coupled to PMDD 14, patient 12 may use one or more fingers, or a hand, for example, to manipulate canister 20 and depress canister 20 with respect to housing 16. In one example, depression of canister 20 may release a dose of medication (determined by the metering valve of canister 20) into a dosing chamber coupled to the valve of PMDD 14. In this case, patient 12 may be required to depress canister 20 for every full dose to be delivered. In other examples, a canister may be used with valve that does not meter doses for each depression of the valve (e.g., a non-metering valve of the canister). In these examples, patient 12 may depress canister 20, and PMDD 14 may include a retaining member for keeping canister 20 in the depressed and open state. In this case, PMDD 14 may also control the valve to open whenever a dose or sub-dose is to be delivered to patient 12 since the metering valve no longer controls doses of medication.

In one example, PMDD 14 or system 10 may generate generating a signal indicative of air flow within a portion of PMDD 14. PMDD 14 may include a sensor configured to generate the signal. The air flow may be present within mouthpiece 18 and/or housing 16. A processor of PMDD 14 may receive a command based on the signal indicative of the air flow, where the command is also associated with a valve of PMDD 14 configured to at least partially control release of medication to patient 12 via PMDD 14. The valve may be coupled to mouthpiece 18 and/or housing 16. In addition, the processor of PMDD 14 may be configured to control, based on the received command, the valve to release at least a portion of a dose of the medication from canister 20 into the air flow within mouthpiece 18 and/or housing 16.

In some examples, the generated signal indicative of air flow may already be calibrated or in a form that can be interperable to represent some parameter of the air flow. For example, the signal may be an analog electrical signal or raw data. In other examples, a sensor module or processor may determine, based on the signal, a parameter value representative of the signal and including a usable value representing one or more conditions of the air flow. In some examples, the parameter value may be indicative of one or more of a flow rate (e.g., cubic meters per second), a velocity (e.g., meters per second), or a pressure of the air through a portion of PMDD 14.

PMDD 14 and/or computing device 22 may generate the command that controls the release of medication through the valve of PMDD 14 based on whether the parameter value has, or has not, exceeded a respective threshold. A threshold may be used by a processor to determine when an inhalation has occurred instead of a non-inhalation movement of air. For example, the threshold may be a threshold flow rate, velocity, or pressure. In response to determining that the detected parameter value is above the threshold, the processor may generate a command to open the valve and release medication into the stream of air. If the parameter value decreases below the threshold, the processor may command the valve to close.

In other examples, or in addition, a processor may generate a command to close the valve after a predetermined period of time has elapsed or a predetermined volume of air has been detected. The processor may track the elapsed period of time, or calculate the volume of air inhaled by the patient by determining the flow rate over time or the detected air flow velocity through a known internal cross-sectional area of PMDD 14 at which the sensor is located. PMDD 14 and/or computing device 22 may provide accurate medication doses or sub-doses by tracking the actual volume air passing through PMDD 14 for which medication was dispensed. In response to determining that the expected volume of air has been inhaled for a particular dose of medication, PMDD 14 and/or computing device 22 may generate a command to close the valve to terminate the dose. Alternatively, if the valve is closed due to low air flow prior to completion of the medication dose, PMDD 14 and/or computing device 22 may control the valve to open again, deliver remaining medication, and continue with this process until the full dose has been delivered to patient 12. In this manner, commands may be generated in response to air flow parameter values falling below a flow rate threshold or velocity threshold and volumes of air flow exceeding respective thresholds. Furthermore, PMDD 14 and/or computing device 22 may calculate the actual volume or amount of substance delivered to patient 12 to reduce the likelihood of medication over-dosing. PMDD 14 and/or computing device 22 may also include a lockout feature that prevents actuation of the valve for a predetermined time period after delivery of a dose to patient 12. Computing device 22 may also control the value to open long enough to dispense a full dose of medication in one continuous delivery of medication.

In some examples, the sensor of PMDD 14, e.g., an air flow sensor or pressure sensor, may generate an electrical signal indicative of the air flow within the portion of PMDD 14 at which the sensor is located (e.g., mouthpiece 18 or housing 16). This electrical signal may be generated as a function of a deformation of an element of the sensor or a mechanical motion of the element of the sensor. Alternatively, the electrical signal may be generated as a function of any change in current in an element of the sensor due to air flow that cools the element.

In other examples, the sensor may produce a detectable visual indication of the air flow within the portion of PMDD 14. The sensor may include a spindle, propeller, or any other element that moves in response to air flow. In some examples, the sensor may also include one or more markings to facilitate detection of element motion. An optical sensor (e.g., a digital camera) of computing device 22 may obtain period images of the element through a transparent portion of mouthpiece 18. Based on the detected movement of the element, computing device 22 may determine a parameter value indicative of the air flow within mouthpiece 18 and generate a command for the valve of PMDD 14 in accordance with the parameter valve. Alternatively, an element of the sensor may be magnetic such that a magnetic field of the sensor changes as the element changes position. A sensor (e.g., a magnetic field sensor or near-field communication module) of computing device 22 may be configured to detect the change in magnetic field and determine the air flow within mouthpiece 18. In some examples, an optical sensor of computing device 22 may be configured to detect air flow by detecting particle movement present within mouthpiece 18.

Alternatively, or in addition, to a sensor in contact with an air flow within PMDD 14, computing device 22 and/or PMDD 14 may include a microphone (e.g., a digital microphone) configured to detect sounds indicative of patient inhalation. In other examples, PMDD 14 may include a membrane or channel that transfers sounds and/or vibrations to the microphone housed by computing device 22 for detection. The act of inhaling typically produces audible sounds associated with air turbulence as the air moves through PMDD 14 and patient 12. A processor may be configured to detect sounds indicative of inhalation, and use these sounds to produce a parameter value representative of air flow within PMDD 14. The processor may compare sound frequency, amplitude, and/or patterns to one or more thresholds or templates to differentiate inhalation sounds from other sounds. In some examples, computing device 22 or PMDD 14 may provide a training mode during which patient 12 provides practice inhalations. Computing device 22 may analyze the practice inhalations to generate an inhalation sound template indicative of inhalation sounds. Subsequent inhalations may be detected by comparing obtained audio data to the inhalation sound template. It is noted that two or more of any inhalation sensors described herein (e.g., air flow sensors, optical sensors, and microphones) may be used to detect inhalations.

As shown in the example of FIG. 1, PMDD 14 is in communication with computing device 22. Computing device 22 may be configured to provide commands to PMDD 14 for controlling the opening and closing of the valve. PMDD 14 may include a communication unit configured for, in response to generating the signal indicative of the air flow within PMDD 14, transmitting the signal to a communication unit of computing device 22. In response to receiving the generated signal from the PMDD 14, computing device 22 may generate the command based on the received signal. In some examples, computing device 22 may first determine a parameter value representative of the signal and/or compare the signal or parameter value to a respective parameter. In this manner, computing device 22 may generate the command based on a parameter value representing the air flow, such as velocity, flow rate, pressure, etc. Computing device 22 may then transmit, via a communication unit, the generated command to PMDD 14. In some examples, the command may include an indication of whether the valve should be open or closed. In other examples, the command may include additional information such as a time period during which the valve is to be opened or closed.

Computing device 22 may include one or more applications that control one or more modules configured to perform various functions related to the control of the PMDD 14 valve, such as a sensor module that determines parameter values and a valve control module that generates valve commands. These one or more applications may be included in a computer-readable storage medium (e.g., storage device of computing device 22). In this manner, the applications may include instructions that, when executed by one or more processors of computing device 22, cause the one or more processors to perform the various functions described herein.

Although PMDD 14 may generally include electronic components that facilitate communication with computing device 22 to obtain commands for controlling the valve, PMDD 14 may independently include processors and/or modules configured to provide the functionality of computing device 22. For example, PMDD 14 may receive the signal indicative of air flow and generate the command for the valve based on the received signal. PMDD 14 may then control the valve to release medication from PMDD 14 without the need for communication with another device.

By controlling the valve to release medication, PMDD 14 may be configured to separate full doses of medication into a plurality of sub-doses each directed to a different inhalation event. In order to direct a sufficient dosage of medication into the lungs, average users may need more than 100-200 milliliters (mL) of air. Air volumes of one or two liters of air would provide better efficiencies and deposit the medication further into the lower airways of the lungs. Since patients may not be able to inhale such large volumes of air, particularly those patients with already narrowed airways, PMDD 14 may be configured to divide the prescribed full dose into approximately 5 to 10, for example, sub-dose portions. Collectively, these sub-doses may create a more desirable two liters or more of inhaled air for each full dose.

In this manner, patient 12 is not required to obtain the full dose in a signal large inhalation. Instead, patient 12 may take a number of smaller, more manageable inhalations, and PMDD 14 will deliver a sub-dose of medication for each of the smaller inhalations. Collectively, the plurality of sub-doses may combine to result in approximately the same amount of medication metered for a single dose from canister 20. The sub-doses may be equal in size or varied to match the flow rate and/or volume of air in each inhalation.

In one example, PMDD 14 may include a dosing chamber (e.g., a tubule) between an orifice through which medication is released from housing 16 and the valve controlled by PMDD 14. The orifice may also be used to create an aerosol mist of the medication to be carried by the air flow. The dosing chamber may be an intermediate reservoir or holding chamber between canister 20 and the valve. When patient 12 depresses canister 20, the full dose of medication is released into the dosing chamber. However, because the valve is closed, the medication is not yet released to patient 12. In response to the detection of an inhalation, PMDD 14 and/or computing device 12 may control the valve to open and allow at least a portion of the dose of medication to be delivered into the air stream of the inhalation. PMDD 14 may continue releasing additional sub-doses to the patient during subsequent inhalations until the full dose has been delivered.

In an alternative example, PMDD 14 may directly release sub-doses to patient 12 without first directing the medication through a dosing chamber. PMDD 14 may include the valve between canister 20 and a structure of housing 16 including the orifice, coupled to the orifice, or positioned in place of the orifice. When canister 20 is depressed, the metering valve of canister 20 opens to release a dose to the valve, and PMDD 14 controls the valve of PMDD 14 to open in response to inhalations to directly deliver sub-doses of medication over time until the full dose is delivered. Alternatively, when canister 20 contains a non-metering valve, depression of canister 20 may open to continually release medication as the valve opens. In this case, PMDD 14 and/or computing device 22 may track the amount of medication dispensed through the sub-doses to create a virtual full dose selected to match the preset dose of canister 20 or match an amount of medication prescribed by a clinician for each dose of medication typically released with a metering valve.

PMDD 14 may include the valve, one or more air flow sensors, or electrical components within housing 16 and/or mouthpiece 18. For example, mouthpiece 18 may include the sensor while housing 16 may include the valve and associated electronics for controlling the valve and, in some examples, communicating with computing device 22. In this manner, housing 16 may be modified from currently available MDIs available for manual dispensing of medication.

Alternatively, mouthpiece 18 may include the functionality described herein as an add-on device to unmodified MDIs (e.g., a commercially available MDI housing). In this manner, housing 16 may be an unmodified housing of typical MDIs for manual dispensing of medication, and mouthpiece 18 may be added as needed to achieve the features described herein. Mouthpiece 18 may be constructed to be removably coupled to a mouthpiece portion, or exit portion, of housing 16. In addition, mouthpiece 18 may include the air flow sensor, the valve, and a dosing chamber coupled to the valve and configured to mate with an orifice of housing 16. Medication from canister 20 may typically be dispensed into an air flow through the orifice. Alternative to the dosing chamber, the valve may be configured to mate directly to the orifice. Mouthpiece 18 may also define one or more intake openings through which at least a portion of the air flow originates.

PMDD 14 and computing device 22 may not need to be coupled together for transmitting data between devices. For example, data may be transmitted across a sufficient distance such that computing device 22 may remain in an article of clothing of patient 12 or otherwise in the vicinity of PMDD 14. In other examples, a flexible connecting band may be used to couple PMDD 14 to computing device 22. In some examples, the flexible connecting band may include one or more wired connections for communication between PMDD 14 and computing device 22. In other examples, a separate wired connection may be provided or PMDD 14 and computing may communicate via one or more wireless communication protocols. Wireless communication may utilize Bluetooth, near-field communication, infrared communication, WiFi protocols, or any other wireless communication standard.

Computing device 22 may utilize any number of additional functions or capabilities to facilitate delivery of medication to patient 12, store usage history of PMDD 14, inform clinicians of changes to medication use, notify patient 12 when to take medication based on a schedule, or notify patient 12 of changes to usage instructed by a clinician. Computing device 22 may also utilize a GPS system to identify the location of patient 12 and, based on known high pollution and/or low air quality areas and/or potentially dangerous high altitudes with lower partial pressures of oxygen, notify patient 12 to preemptively take another dose of medication. Computing device 22 may also notify a health care provider (e.g., a clinician) of the patient's usage history. Computing device 22 may transmit data to the health care provider via a network (e.g., wireless networks, cellular networks, the Internet, or any other means) to facilitate remote monitoring of patient condition or compliance by the health care provider. In response to such monitoring, the health care provider may transmit information to computing device 22 and/or the patient to optimize medication administration or other therapies according to patient usage patterns and clinical symptoms.

In other examples, PMDD 14 may be constructed for different breathing situations. For example, PMDD 14 may include an apparatus to direct the air flow to the nose or nose and mouth (e.g., an inhalation mask). PMDD 14 may alternatively be constructed to direct the medication into a breathing circuit or breathing tube that may be used when patient 12 is intubated. In this manner, PMDD 14 and, in some examples, computing device 22, may be configured to deliver medication to any type of air flow during a patient inhalation.

Canister 20 may contain medication in any number of forms. Canister 20 may contain a pressurized substance, non-pressurized liquid, or a powder substance, for example. When canister 20 contains a pressurized substance, the pressurized substance may be released through an orifice pass area that creates an aerosol. In the case of a non-pressurized substance, PMDD 14 may include an electro-mechanical or active mechanism configured to inject or otherwise provide the substance into the stream of air. A perforated barrier may be selectively placed in housing 16 to contain the particles of medication. For example, the mechanism or force, along with the barrier, creates a process that atomizes the aerosol particles of the substance (e.g., into a soft mist) to facilitate a more efficient absorption of the substance in the lower airways. The configuration of the barrier may at least partially control the particle size intended for patient 12.

In this manner, PMDD 14 may be configured to deliver various substances to patient 12. For example, PMDD 14 may be configured to aerosolize a substance originating from a pressurized canister. PMDD 14 may aerosolize the substance from a pressurized or non-pressurized canister in the form of soft mist. PMDD 14 may also be configured to aerosolize a substance originating from a non-pressurized liquid canister. PMDD 14 may alternatively be configured to dispense a substance in the form of dry powder, originating from a dry powder inhaler or canister. According to these descriptions, in some examples, mouthpiece 18 may be configured to couple with a pressurized MDI, a dry powder inhaler (DPI), a small-volume nebulizer (SVN), or a soft mist inhaler (SMI).

If the medication originates from a non-pressurized canister, PMDD 14 may provide a force or action to the medication to deliver it into the air flow towards patient 12. For example, PMDD 14 may include an elastically deformable drive element (e.g., a spring or electro-mechanical device) that delivers the non-pressurized substance. In some cases, the elastically deformable drive element may be compressed into a high energy state prior release that causes the substance to the delivered. An elastically deformable drive element may include a solenoid valve, in some examples. In addition, the valve controlled by PMDD 14 to deliver any type of substance may be a solenoid valve.

The substance delivered to patient 12 using PMDD 14 may include any medication, drug, potentially therapeutic substance, or any combination thereof. Example substances may include beta-adrenergic agonists (e.g., terbutaline), chromoglycin, anticholinergic drugs, and various steroids. In some examples, the substance delivered to patient 12 using PMDD 14 may include any vaccine with or without carriers and/or adjuvant, or any combination thereof, insulin, or any other compound deliverable to the nasal passages, mouth, or lungs. In other examples, the substance selected for delivery to patient 12 using PMDD 14 may be used for the treatment of any condition. Example conditions may include asthma and chronic obstructive pulmonary disease.

In some examples, the substance selected for delivery to patient 12 using PMDD 14 may delivered into the airway of patient 12 in a form selected from the group including a powder, a granule, a cachet, a capsule, a tablet, a paste, a cream, a gel, an ointment, a salve, a foam, a paste, a lotion, a cream, an oil suspension, a spray, a suspension, a solution, an emulsion, a patch, a stick, a spray, preferably a nasal spray, or a buccal spray, a mouth wash, an aerosol, in a venture effect, a drink, and a solution. PMDD 14 may include an aperture or active device to facilitate the delivery of such a form of the substance.

As described herein, PMDD 14 may control a valve to open in response to an inhalation being detected. However, this process may require electrical power from a battery or other batter source. One or more safety features may be implemented to still allow patient 12 access to medication from canister 20 in situations where power is not available to PMDD 14 and/or computing device 22 to operate the valve of PMDD 14. For example, the valve may be constructed such that the valve remains open in the absence of operational power. In another example, PMDD 14 and/or computing device 22 may set the valve to an open configuration after the dose of medication has been delivered. PMDD 14 and/or computing device 22 may then control the valve to close prior to delivering another dose to patient 12 at a subsequent time. In any case, PMDD 14 and/or computing device 22 may be configured to allow patient 12 access to medication even if PMDD 14 and/or computing device 22 are non-functional.

Housing 16 and/or mouthpiece 18 may be constructed of a polymer, composite, metal alloy, or any combination thereof. The materials used to construct housing 16 and/or mouthpiece may be selected not to react with any medication to be dispensed from canister 20. In this manner, the materials may be selected to be bio-compatible, and in some examples, sterilizable. Although housing 16, mouthpiece 18, and any other components contained therein (e.g., a valve, a sensor, and electronics) may be constructed to be reusable between multiple different canisters 20, for example, any or all of PMDD 14 may be constructed to be disposable.

Figure 12:
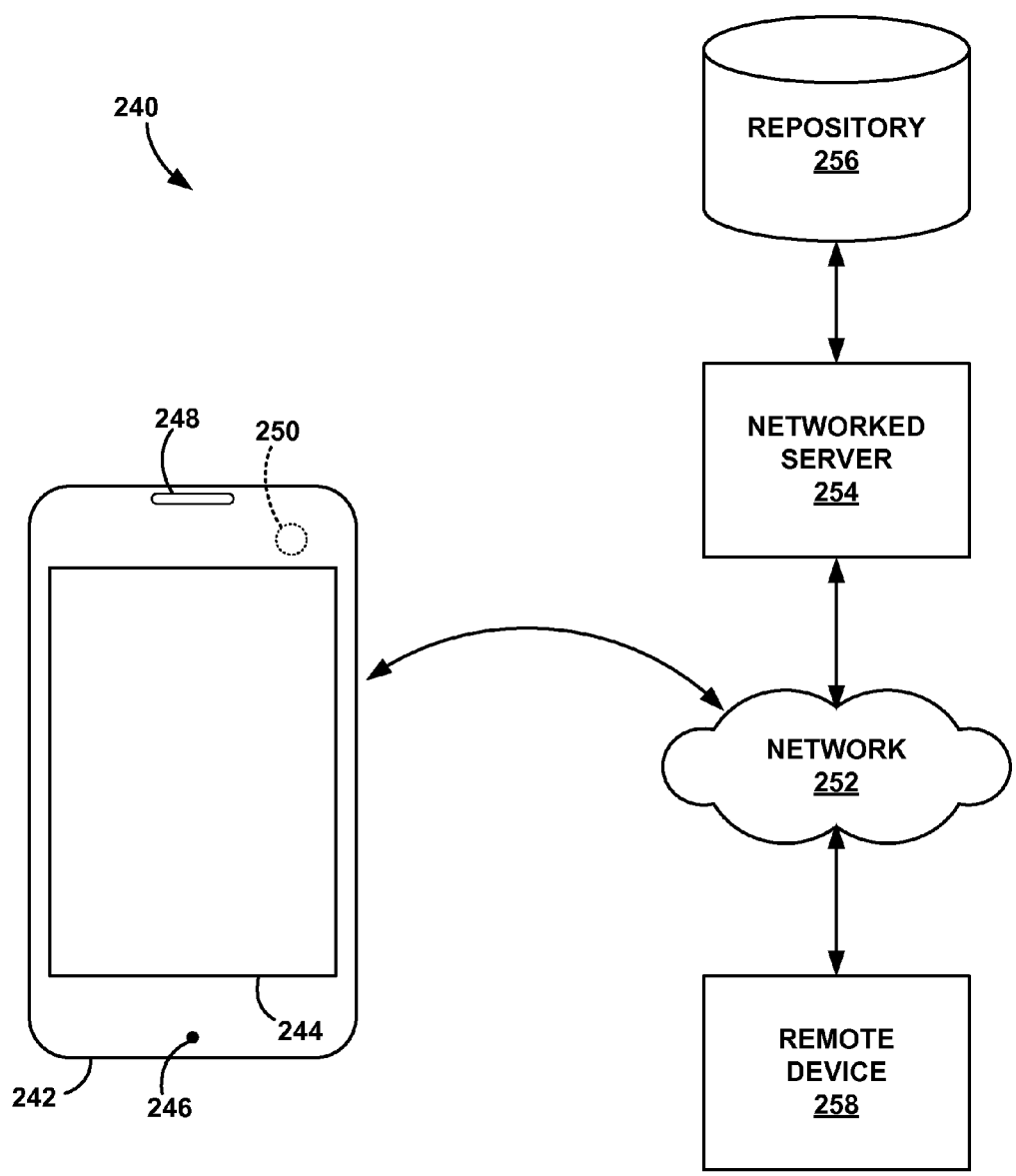
FIG. 12 is a conceptual diagram of an example system that includes a computing device and a networked server associated with use of a PMDD.

Computing device 22 may be any computing device configured to communicate with PMDD, generate a command to control the state of the valve of PMDD 14, and/or deliver additional functionality related to the treatment of one or more conditions of patient 12. For example, computing device 22 may be a mobile device (e.g., a smartphone, a tablet computer, a smartwatch, a notebook computer, a digital camera, or a portable medical device) or a stationary workstation or desktop computer. In any case, computing device 22 may be configured to communicate with a communication unit of PMDD 14 using wired or wireless communication protocols. In addition, computing device 22 may be configured to communicate with a networked server, networked repository, or remote device via a network (as shown in FIG. 12). In some examples, computing device 22 may transmit data (e.g., to a network server) and receive an analysis of the data, a command based on the transmitted data, or any other information to offload processing functions to the networked server or utilize additional features of the networked server (e.g., access to additional data stored on the network or additional processing power).

Figure 2A:
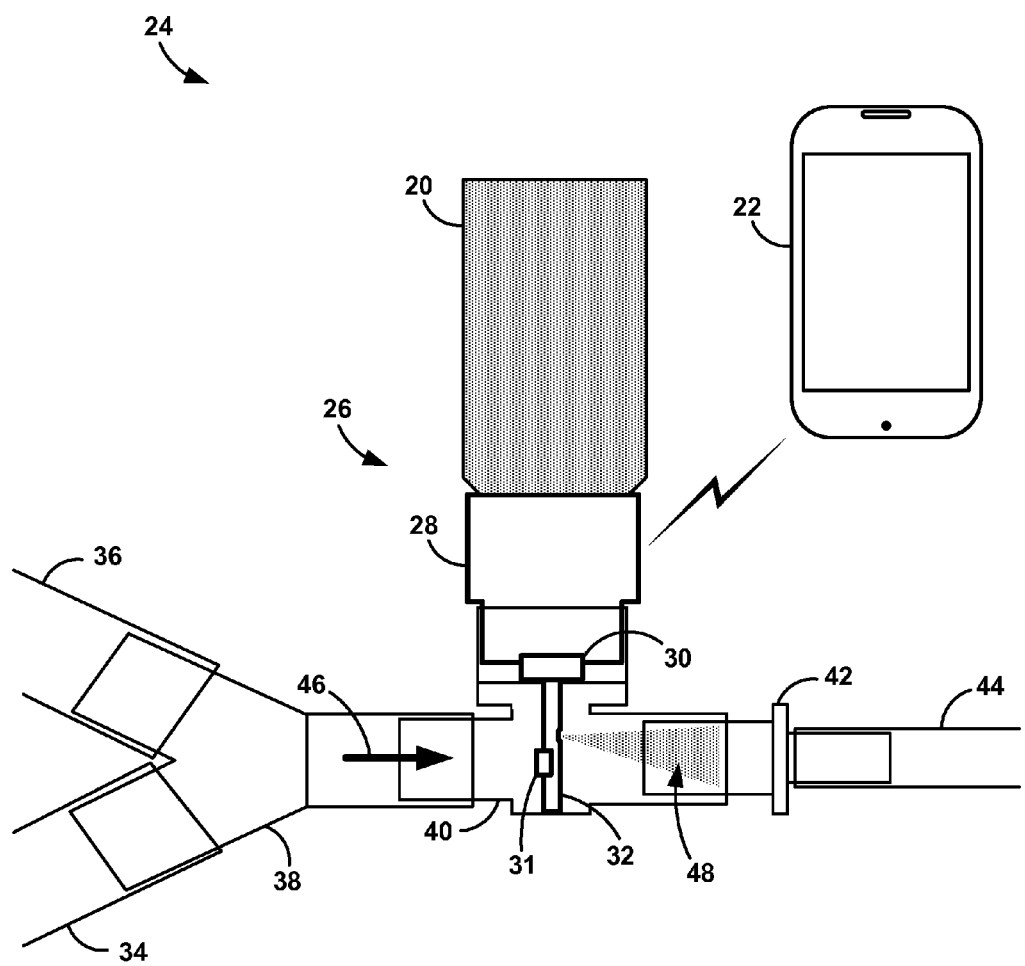
FIGS. 2A and 2B are conceptual drawings illustrating example PMDDs configured to be used within a breathing circuit attached to the user.
Figure 2B:
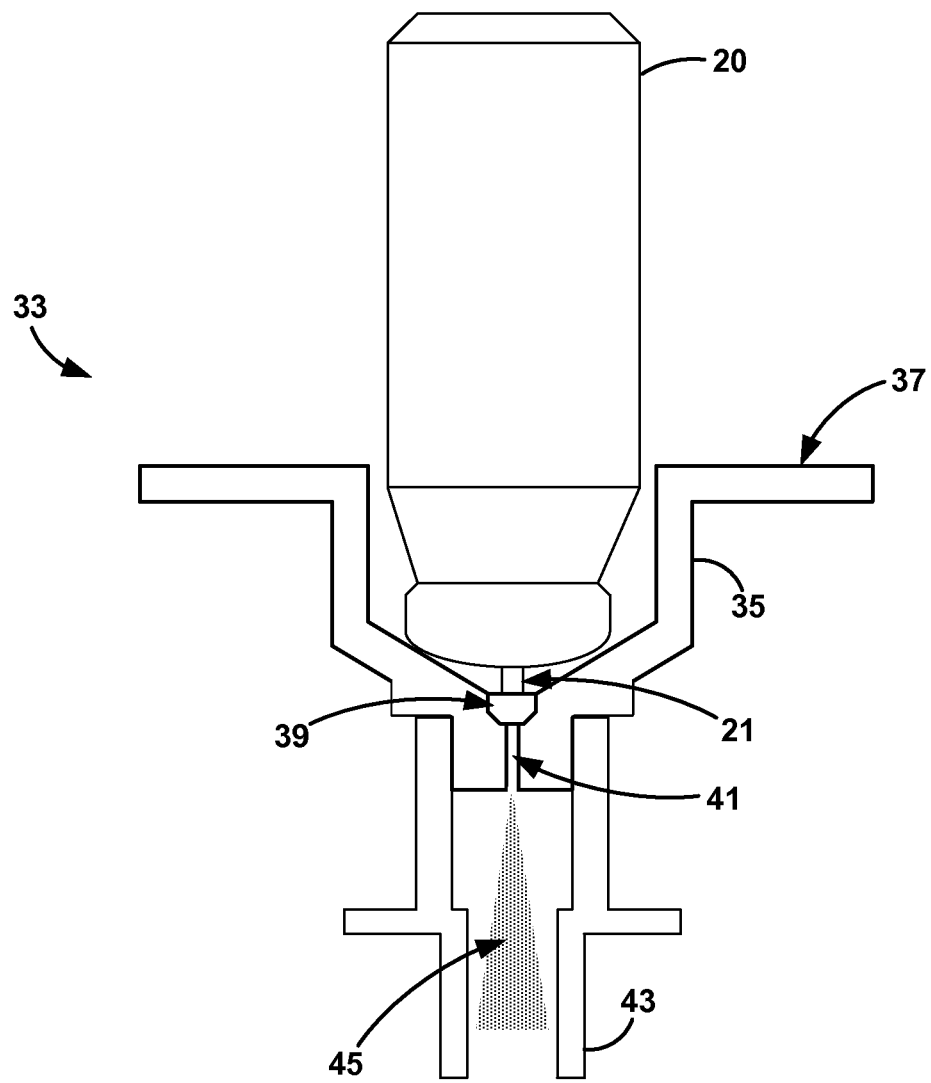

FIGS. 2A and 2B are conceptual drawings illustrating example PMDDs (similar in function to PMDD 14 of FIG. 1) configured to be used within a breathing circuit attached to the patient. As shown in FIG. 2A, system 24 includes PMDD 26, computing device 22, and various components of a breathing circuit coupled to a patient and a ventilator or other assisted breathing system. Tubing 44 may lead into the trachea of the patient (not shown), and adapter 42 may include a portion configured to fit within tubing 44. Tubing 36 and tubing 34 may lead to the ventilator, where tubing 36 is an inflow portion directing air flow towards the patient and tubing 34 is an outflow portion directing air flow away from the patient. T-adapter 38 may couple tubing 36 and tubing 34 to connector 40.

In some examples, a ventilator attached to the breathing circuit may provide periodic inflow to support inhalation by patient 12. In other examples, a ventilator or other breathing support mechanism may provide constant positive pressure that results in continual air flow towards patient 12 in the direction of arrow 46. The air flow may be delivered to a mask through which patient 12 breathes. During this constant air flow, detecting patient inhalation may be done by detecting changes in pressure and/or differences in air flow velocity or flow rate. In other examples, an additional tube may provide a circuit between the patient's mask and the sensor of PMDD 26 such that an inhalation by patient 12 creates a detectable air flow at the sensor of PMDD 26. PMDD 26 and/or computing device 22 may detect changes in air pressure and, based on the air pressure changes, determine one or more breathing patterns of patient 12. PMDD 26 and/or computing device 22 may this determine, based on the breathing patterns, whether the patient is breathing spontaneously or whether the patient is being ventilated. PMDD 26 and/or computing device 22 may use the detected air pressures to, for example, identify air pressure waveforms, determine changes to an air pressure waveform, and control PMDD 26 to administer the medication in response to determining that a change to an air pressure waveform is indicative of an inhaled breath.

PMDD 26 may be similar to PMDD 14 of FIG. 1. PMDD 26 may include housing 28 configured to accept canister 20. Housing 28 may also be coupled to valve 30 for controlling the release of medication from canister 20. In addition, dispensing member 32 is coupled to valve 30 such that medication released from valve 30 is directed out of an orifice defined by dispensing member 32. Air flow sensor 31 may be coupled to dispensing member 32 such that sensor 31 is disposed within the air flow towards the patient. Housing 28 is also coupled to connector 40 such that PMDD 26 can be inserted into, and coupled with, the breathing circuit tubing. As shown, PMDD 26 may control valve 30 to dispense doses or sub-doses to the patient (e.g., dispersed medication 48). Although PMDD 26 is described without a dosing chamber for dividing a full dose into sub-doses, PMDD 26 may include a dosing chamber in other examples.

In the example of FIG. 2A, the patient or ventilator may initiate an inhalation with air flow in the direction of arrow 46. Sensor 31 may generate a signal indicative of the air flow, and a PMDD 26 may transmit the signal, or data indicative of the signal, to computing device 22. As described herein, computing device 22 may receive the signal and generate a command for the valve to control the release of medication from canister 20. Computing device 22 may then transmit the command to PMDD 26 such that PMDD 26 can control valve 30 to open and/or close according to the command. Opening of valve 30 may result in dispersal of medication 38 into the air flow and in the direction of inhalation flow within the breathing circuit.

In some examples, a canister 20 having a metering valve may be provided to release a dose of medication to PMDD 26 for each depression of the canister. In other examples, canister 20 be constructed with a non-metering valve and may remain depressed during delivery of medication from PMDD 26 to the patient. The patient or a clinician may manually maintain depression of canister 20 such that medication can be released. Alternatively, PMDD 26 may include one or more mechanisms (e.g., a latch or retainer bar) configured to maintain canister 20 in the depressed configuration so that the non-metering valve of the canister remains open.

PMDD 33 of FIG. 2B may also be used in a type of breathing circuit or tube used by the patient to inhale air. As shown in the cross-sectional illustration of FIG. 2B. PMDD 33 may function similarly to PMDD 26 of FIG. 2A. PMDD 33 may include housing 35 that defines handle portion 37 and dispensing nozzle 41. PMDD 33 also includes valve 39 that couples to metering valve 21 of canister 20. As canister 20 is depressed towards valve 39 such that metering valve 21 opens, PMDD 33 may control valve 39 to open and release medication 45 through dispensing nozzle 41 and into a breathing circuit. PMDD 33 is configured to mate with connector 43, and connector 43 may be configured to couple with an intubation tube and/or breathing circuit such as the circuit described in FIG. 2A.

In some examples, a canister 20 having a metering valve 21 may be provided to release a dose of medication to PMDD 33 for each depression of the canister. In other examples, canister 20 constructed with a non-metering valve may remain depressed to continuously deliver medication from PMDD 33 to the patient. The patient or a clinician may manually depress canister 20 such that medication can be released. Alternatively, PMDD 33 may include one or more mechanisms (e.g., a latch or retainer bar) configured to maintain canister 20 in the depressed configuration so that a non-metering valve of the canister remains open. In some examples, housing 35 may include a collar or other narrow portion within which canister 20 is inserted. The collar may provide a force against a shoulder of canister 20 such that canister 20 remains in the depressed configuration and the non-metering valve is open in these alternative examples.

Figure 3:
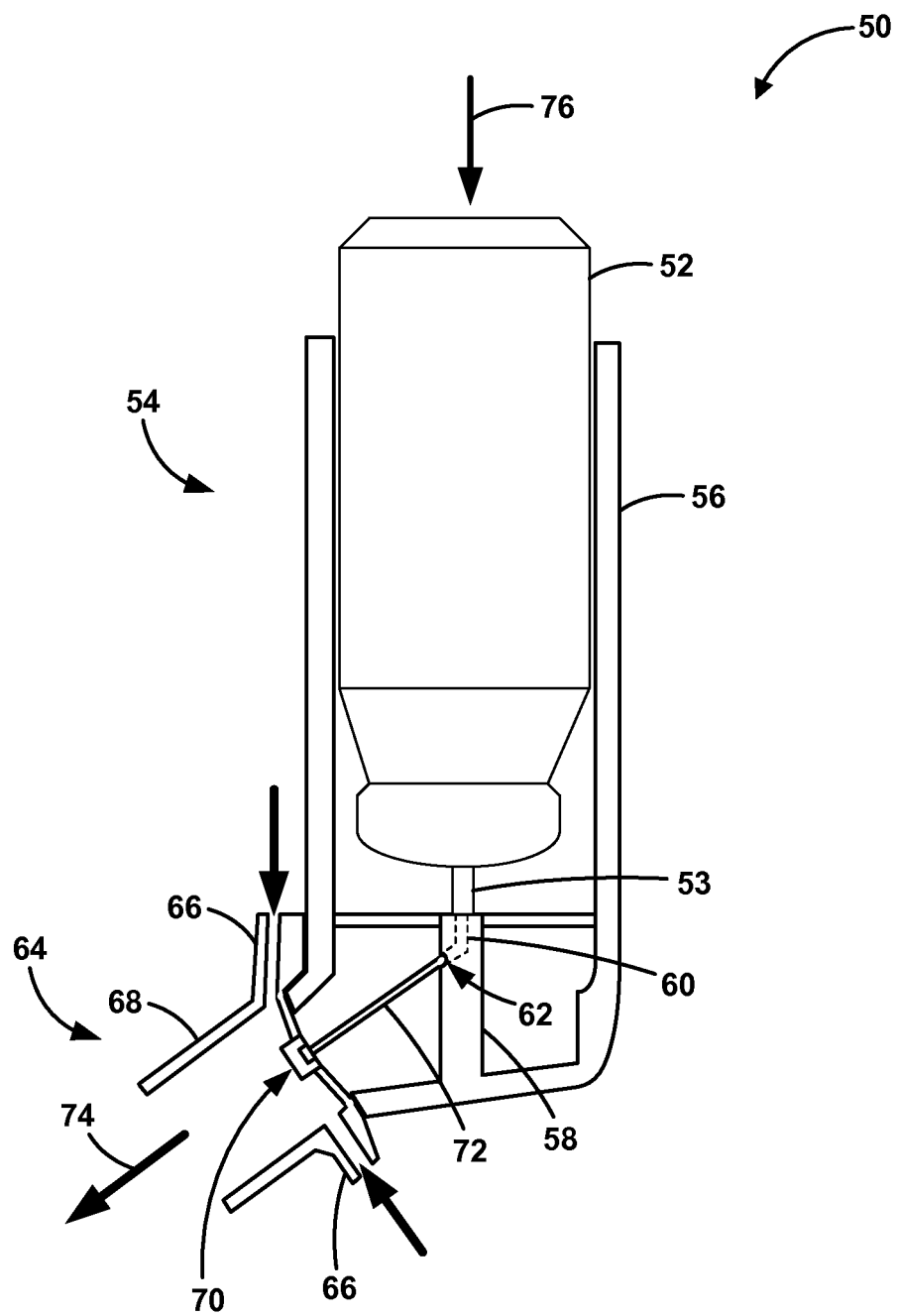
FIG. 3 is a conceptual drawing illustrating an example PMDD having a dosing chamber coupled to a valve.

FIG. 3 is a conceptual drawing illustrating a cross-section of an example PMDD 50 having dosing chamber 72 coupled to valve 70. PMDD 50 may be an example of PMDD 14 of FIG. 1. As shown in FIG. 3, PMDD 50 includes housing 54 coupled to mouthpiece 64. Housing 54 includes canister portion 56 for accepting medication canister 52 and structure 58 that accepts metering valve 53 of canister 52. Structure 58 also defines channel 60 and orifice 62, wherein medication dispensed from canister 52 is directed through channel 60 and out of orifice 62. Without mouthpiece 64, housing 54 may function similar to a manually operated MDI by depressing canister 52 in the direction of arrow 76.

However PMDD 50 also includes mouthpiece 64 attached to housing 64. Mouthpiece 64 may be a delivery portion of PMDD 50 and include functional components such as valve 70, a sensor (shown combined with valve 70), dose chamber 72, and related electronics. In this manner, mouthpiece 64 may be an add-on device to transform the operation of housing 54 into PMDD 50 configured to dispense medication in response to detected inhalation and deliver sub-doses of the medication. However, both housing 52 and mouthpiece 64 may be configured to function together.

Mouthpiece 64 may include a nozzle portion 68 shaped and sized to direct air flow to mouth 13 of patient 12. Mouthpiece 64 may also include valve 70. Intake portions 66 of mouthpiece 64 define respective intake openings in mouthpiece 64. Intake portions 66 direct air from outside of PMDD 50, toward the location of valve 70 and the associated sensor, and out of nozzle portion 68 to mouth 13 of patient 12. Although two intake openings are shown in mouthpiece 64, mouthpiece 64 may alternatively be constructed to define only one intake portion or more than two openings. The cross-sectional area of the intake openings may be sized to facilitate appropriate air flow rates through mouthpiece 64. In some examples, mouthpieces with smaller intake openings may be constructed from younger patients in comparison with larger openings for adults. In addition, or alternatively, to intake portions 66, housing 54 may define or more intake openings for drawing air through a portion of housing 54 behind the location of valve 70.

Valve 70 may be positioned near the axis running through the center of nozzle portion 68. Although valve 70 may be positioned at any location within or near mouthpiece 64, a generally center position of valve 70 may increase the amount of medication distributed to the air stream. A sensor may be combined with valve 70, such adjacent to or surrounding the valve. However, the sensor may be positioned at any location in which the air flow may be sensed. Valve 70 is also coupled to dosing chamber 72. Dosing chamber 72 may be configured as a tubule, although any size and shape (e.g., funnel shapes, rectangular shapes, curved shapes, etc.) may be selected. Dosing chamber 72 may be fitted within orifice 62 or otherwise mated to orifice 62 such that the dose of medication released out of canister 52 will be trapped within dosing chamber 72 until valve 70 is opened. For a pressurized canister, the medication would remain pressurized within dosing chamber 72. For non-pressurized canisters, valve 70 may actively eject the sub-doses of medication or an active element may provide the force necessary to place the medication within the air flow moving across valve 70.

Mouthpiece 64 may also include an electronics package configured to sense air flow, control valve 70, and/or transmit data to a computing device that at least partially controls valve 70. The electronics package may also include a power source, such as a rechargeable battery or non-rechargeable battery. The electronics may be disposed inside of mouthpiece 64 and/or on an external surface of mouthpiece 64.

Mouthpiece 64 may be removably attached to housing 54. In other words, mouthpiece 64 may be added to housing 54 when needed, removed from housing 54, reattached to housing 54, or attached to a different housing. Mouthpiece 64 may be attached to housing 54 using a friction fit, an adhesive, fastening devices, indent/detent connections, helical fittings, or any other mechanism. Mouthpiece 64 may be constructed of a rigid, flexible, elastic, transparent, clear, and/or opaque material. In some examples, mouthpiece 64 may be constructed of several different materials, each material directed to a specific feature or as different layers of mouthpiece 64.

Patient 12 may use PMDD 50 by first connecting mouthpiece 64 to housing 54 such that dosing chamber 72 mates with orifice 62. Patient 12 may then place nozzle portion 68 into mouth 13 and depress canister 52 in the direction of arrow 76 to release a dose of medication into dosing chamber 72. Subsequently, patient 12 inhale air such that air flows in the direction of arrows 74. In response to a signal from the sensor indicating the air flow, PMDD 50 may control valve 70 to open and release a sub-dose of medication from dosing chamber 72. In some examples, the sub-dose may be predetermined by a predetermined duration in which valve 70 is opened before being closed. In other examples, PMDD 50 may keep valve 70 open as long as a parameter value representative of the air flow remains above a threshold (e.g., as long as the inhalation continues). Canister 52 may be depressed a single time to provide a single dose into dosing chamber 72, or canister 52 may be retained in the depressed position (e.g., manually by patient 12 or by a mechanism of PMDD 50).

Figure 4:
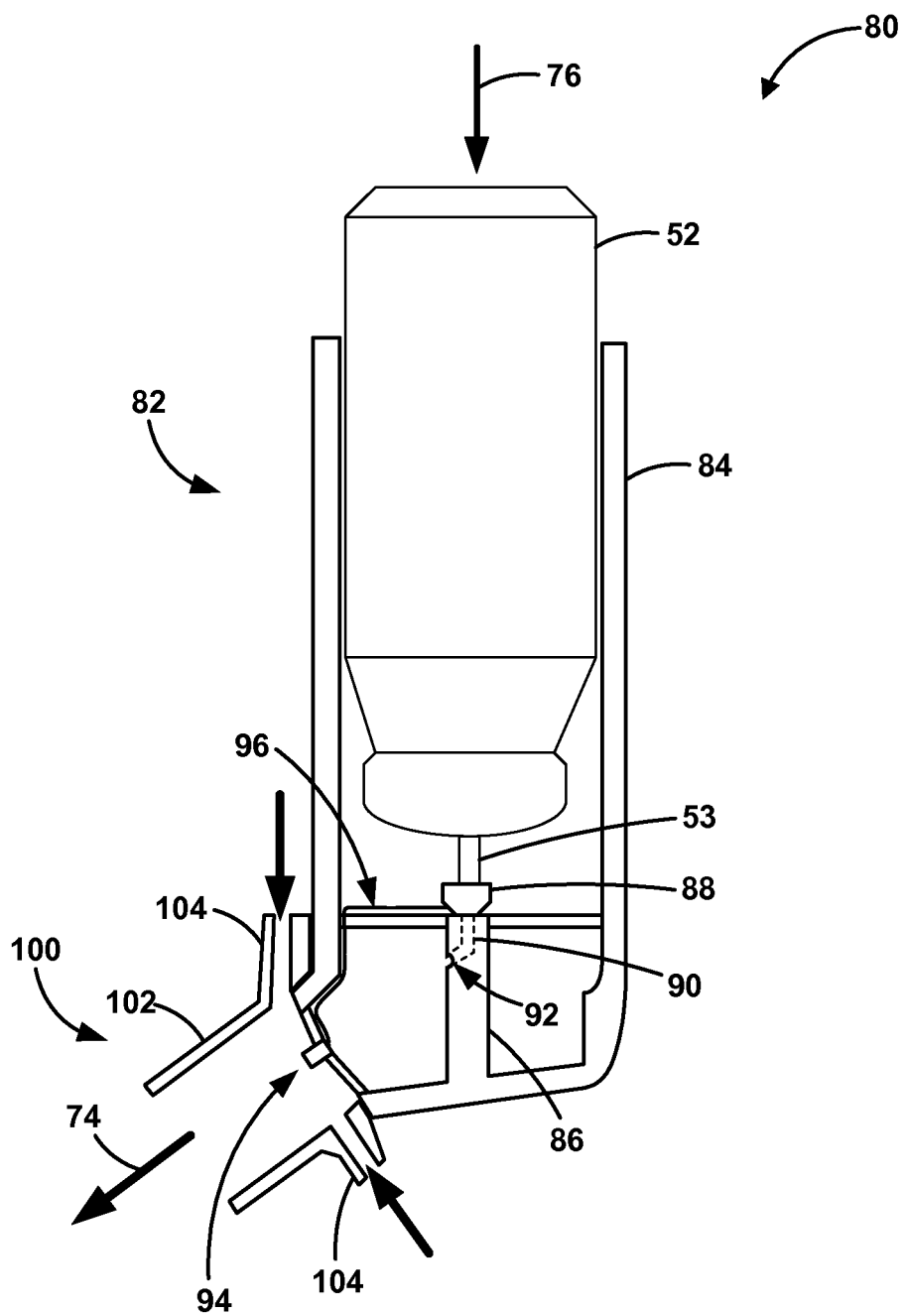
FIG. 4 is a conceptual drawing illustrating an example PMDD having a valve configured to release medication directly from a medication canister.

FIG. 4 is a conceptual drawing illustrating a cross-section of an example PMDD 80 having valve 88 configured to release medication directly from medication canister 52. PMDD 80 may be substantially similar to PMDD 50 of FIG. 3. However, PMDD 80 is constructed without the use of a dosing chamber to segment sub-doses from full doses of medication. Instead, valve 88 is controlled to directly determine the sub-doses of medication delivered during an opening of metering valve 53 to valve 88. In examples in which valve 53 is a non-metering valve, valve 88 may be controlled to directly determine sub-doses and virtual full doses from a continually opened valve.

As shown in FIG. 4, PMDD 80 includes housing 82 coupled to mouthpiece 100. Housing 82 includes canister portion 84 for accepting medication canister 52 and structure 86 that accepts metering valve 53 of canister 52. Structure 86 also defines channel 90 and orifice 92, wherein medication dispensed from canister 52 is directed through channel 90 and out of orifice 92. PMDD 80 also includes valve 88 coupled to structure 86 and configured to accept metering valve 53. In this manner, valve 88 may provide for fluid communication between metering valve 53 and channel 90. Housing 82 also includes sensor 94 coupled to an electronics package within housing 82 via cable 96. Sensor 94 may generate a signal indicative of air flow during an inhalation, based on which PMDD 80 may control valve 88.

PMDD 80 also includes mouthpiece 100 attached to housing 82. Mouthpiece 100 may be a delivery portion of PMDD 80. Mouthpiece 100 may include a nozzle portion 102 shaped and sized to direct air flow to mouth 13 of patient 12. Intake portions 104 of mouthpiece 100 define respective intake openings in mouthpiece 100. Intake portions 104 direct air from outside of PMDD 80, toward the location of valve sensor 94, and out of nozzle portion 102 to mouth 13 of patient 12.

Mouthpiece 100 may be removably attached to housing 82. In other words, mouthpiece 100 may be added to housing 82 when needed, removed from housing 82, reattached to housing 82, or attached to a different housing. Mouthpiece 100 may be attached to housing 82 using a friction fit, an adhesive, fastening devices, indent/detent connections, helical fittings, or any other mechanism. Mouthpiece 100 may be constructed of a rigid, flexible, elastic, transparent, clear, and/or opaque material. In some examples, mouthpiece 100 may be constructed of several different materials, each material directed to a specific feature or as different layers of mouthpiece 100.

Patient 12 may use PMDD 80 by first connecting mouthpiece 100 to housing 82. Patient 12 may then place nozzle portion 102 into mouth 13 and depress canister 52 in the direction of arrow 76 to open metering valve 53 and release a full dose to valve 88. Subsequently, patient 12 inhale air such that air flows in the direction of arrows 74. In response to a signal from sensor 94 indicating the air flow, PMDD 80 may control valve 88 to open and release a sub-dose, or at least a portion of a full dose, of medication from orifice 92, past sensor 94, and into air flow within mouthpiece 100. PMDD 80 may, in other examples, control value 88 to open and release the full dose in one continuous delivery of medication. In some examples, housing 82 may include a latch or other mechanism to retain canister 52 in the depressed configuration if a non-metering valve is used for canister 52.

Figure 5:
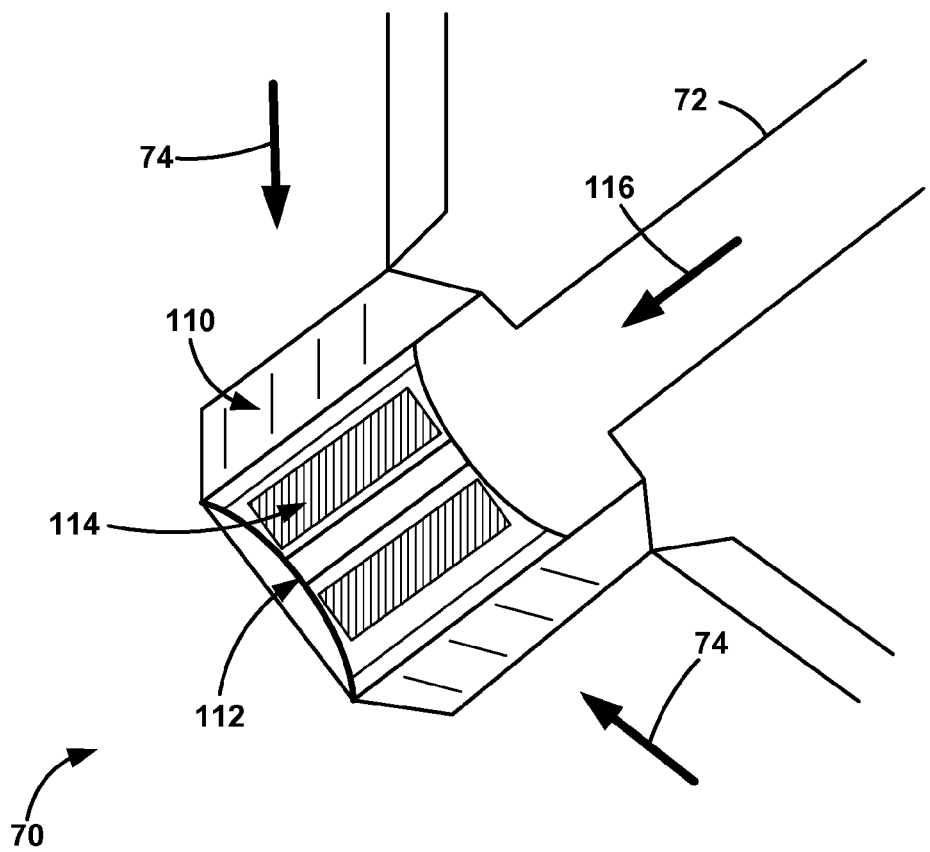
FIG. 5 is a conceptual drawing illustrating an example valve and sensor of the PMDD of FIG. 3.

FIG. 5 is a conceptual drawing illustrating an example valve 70 and sensor 110 of PMDD 50 of FIG. 3. As shown in FIG. 5, valve 70 may include seal 112 that opens in response to control from PMDD 50. Sensor 110 is illustrated as a spindle for detecting air flow in the direction of arrows 74. Sensor 110 may have one or more wings or vanes to which pressure from the air flow is applied. This pressure is a force that causes the sensor to spin at a rate indicative of the air flow velocity. Electronic package 114 may be retained within valve 70 and may include one or more processors and/or power sources for generating a signal indicative of the air flow detected by sensor 110 and controlling the opening and closing of valve 70.

A dose of medication may be stored within dosing chamber 72. In response to sensor 110 indicating that air is flowing in the direction of arrows 74, PMDD 50 may control valve 70 to open and release the medication from dosing chamber 72 in the direction of arrow 116. Valve 70 may be an electro-mechanical valve that uses an electrical signal to modulate a mechanical opening. An example electro-mechanical valve may be a solenoid valve, in some examples. Valve 70 may be implemented in a PMDD with or without a dosing chamber 72.

Figure 6:
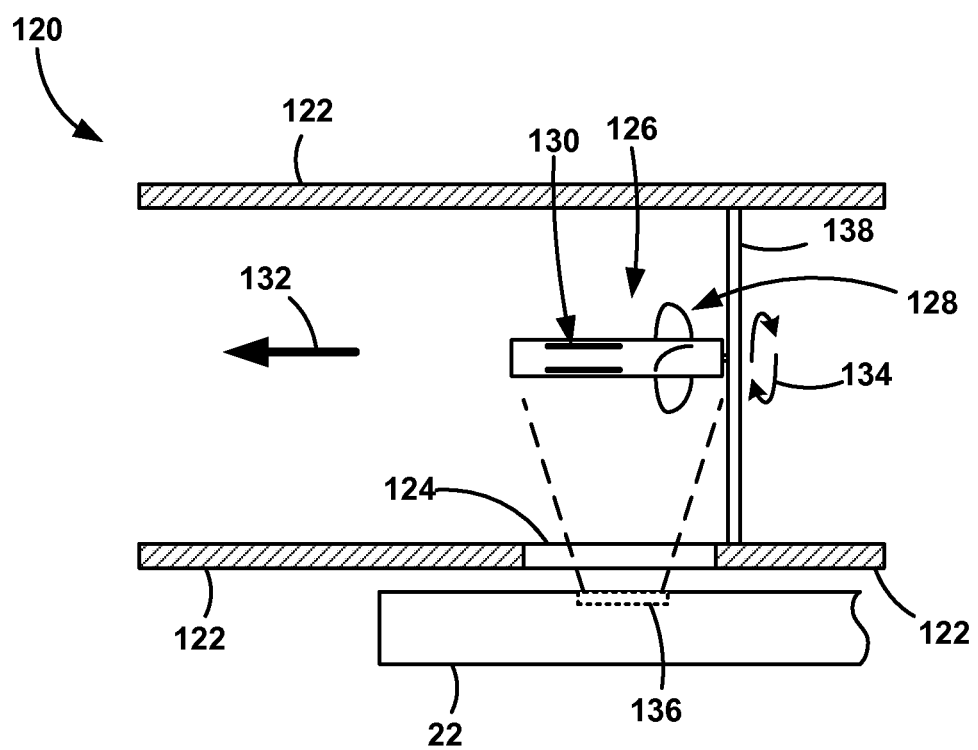
FIG. 6 is a conceptual drawing illustrating an example sensor within a mouthpiece of a PMDD visually detectable by a computing device.

FIG. 6 is a conceptual drawing illustrating an example sensor 126 within a mouthpiece 120 of a PMDD visually detectable by computing device 22. As shown in the example of FIG. 6, sensor 126 may not be electrically coupled to any circuit for generation of a signal indicative of air flow in the direction of arrow 132. Instead, sensor 126 may rotate or spin in the direction of arrows 134 within a flow of air, and an optical sensor 136 may obtain images indicative of the rotating sensor.

Mouthpiece 120 may be similar to mouthpiece 18 of FIG. 1 and configured to attach to a housing containing a medication canister. Mouthpiece 120 may include walls 122 to form an inner channel in which sensor 126 is located. Sensor 126 may be constructed of a cylinder comprising a plurality of blades 128 and, in some examples, visual markings 130 around the circumference of sensor 126. Sensor 126 may be coupled to support 138 via a pin or other fastener that allows sensor 126 to spin. Support 138 may retain sensor 126 within the air flow of an inhalation from the patient.

When air flows through mouthpiece 120 in the direction of arrow 132, force from the air flow is applied to blades 128 and causes sensor 126 to rotate in the direction of arrows 134. The rotation of sensor 126 is visually detectable by computing device 22. Window 124 may be a transparent portion of the exterior wall of mouthpiece 120 that allows light to leave mouthpiece 120. Computing device 22 may control optical sensor 136 to obtain a series of images and analyze the images for any movement of blades 128 and/or markings 130. In response to determining that sensor 126 is rotating, computing device 22 may generate and transmit a command to the PMDD to open the valve to release medication into the inhalation air flow. In this manner, PMDD may not need to transmit any signal indicative of air flow within mouthpiece 120 because computing device 22 can independently determine when an inhalation is occurring.

Figure 7:
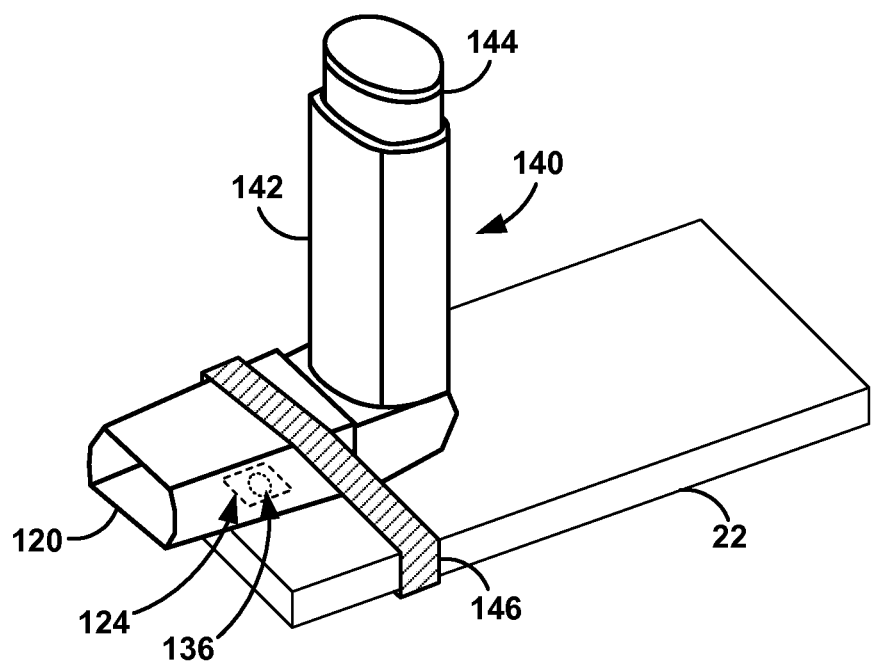
FIG. 7 is a conceptual drawing illustrating an example configuration of a PMDD coupled to a mobile computing device configured to detect air flow.

FIG. 7 is a conceptual drawing illustrating an example configuration of PMDD 140 coupled to mobile computing device 22 that is configured to detect air flow within PMDD 140. PMDD 140 may be similar to PMDD 16 of FIG. 1. Mouthpiece 120 of FIG. 6 may be coupled to housing 142, and medication canister 144 may be accepted within housing 142. Mouthpiece 120 includes window 124 that is at least partially transparent. Retaining band 146 may contact a portion of mouthpiece 120 and a portion of computing device 22 to retain PMDD 140 against computing device 22. Retaining band 146 may also maintain an alignment of window 124 over optical sensor 136 of computing device 22. In this manner, optical sensor 136 may obtain images of sensor 126 within mouthpiece 120 for determining when inhalation hair flow begins.

Retaining band 146 may be at least partially elastic, include one or more clasps, or any other fasteners that maintain a secure connection between PMDD 140 and computing device 22. In some examples, retaining band 146 may include a wired connection to directly transmit data between PMDD 140 and computing device 22. In other examples, a case for computing device 22 may include a pocked sized to accept mouthpiece 120 against computing device 22 and align window 124 to optical sensor 136 of computing device 22. In any example, a device may be used to retain computing device 22 against PMDD 140. Computing device 22 may initiate the visual detection method using optical sensor 136 in response to receiving an input from the patient that an inhalation will occur. In some examples, window 124 may be a lens or other structure that changes the focal length of optical sensor 136 to visually focus on a sensor within mouthpiece 120 and/or droplets within an air flow of mouthpiece 120.

In other examples, optical sensor 136 may be used to detect air flow by imaging droplets or particles within the air flow. In some examples, optical sensor 136 may be configured to obtain images during inhalation, and computing device 22 may be configured to count drug droplets or particles within the inflow of medication to determine the amount of medication being delivered to the patient. Alternatively, an electrical sensor may be used to count the medication droplets or particles within the air flow, such as impedance changes due to changes in moisture and/or density of the air.

Furthermore, computing device 22 may be configured to estimate the amount of medication inhaled, exhaled, and/or retained by the patient. For example, using optical sensor 136, computing device 136 may count medication droplets and/or determine density changes in the air indicative of the amount of medication within the inhaled and exhaled air. Computing device 22 may determine the direction of air flow to determine if the medication is being inhaled or exhaled. In some examples, computing device 22 may determine the amount of medication retained in the lungs of the patient subtracting the amount of medication detected in the exhalation from the amount of medication detected in the immediately preceding inhalation. In other words, the amount of medication detected in the exhalation is medication that was not retained within the lungs. Computing device 22 may store the inhaled medication amount, the exhaled medication amount, and/or the determined difference between the inhaled and exhaled medication amount for later review by the patient and/or clinician. This information may be used to evaluate the function of PMDD 140, the delivery technique of the user, and/or investigate efficacy of the medication.

Figure 8:
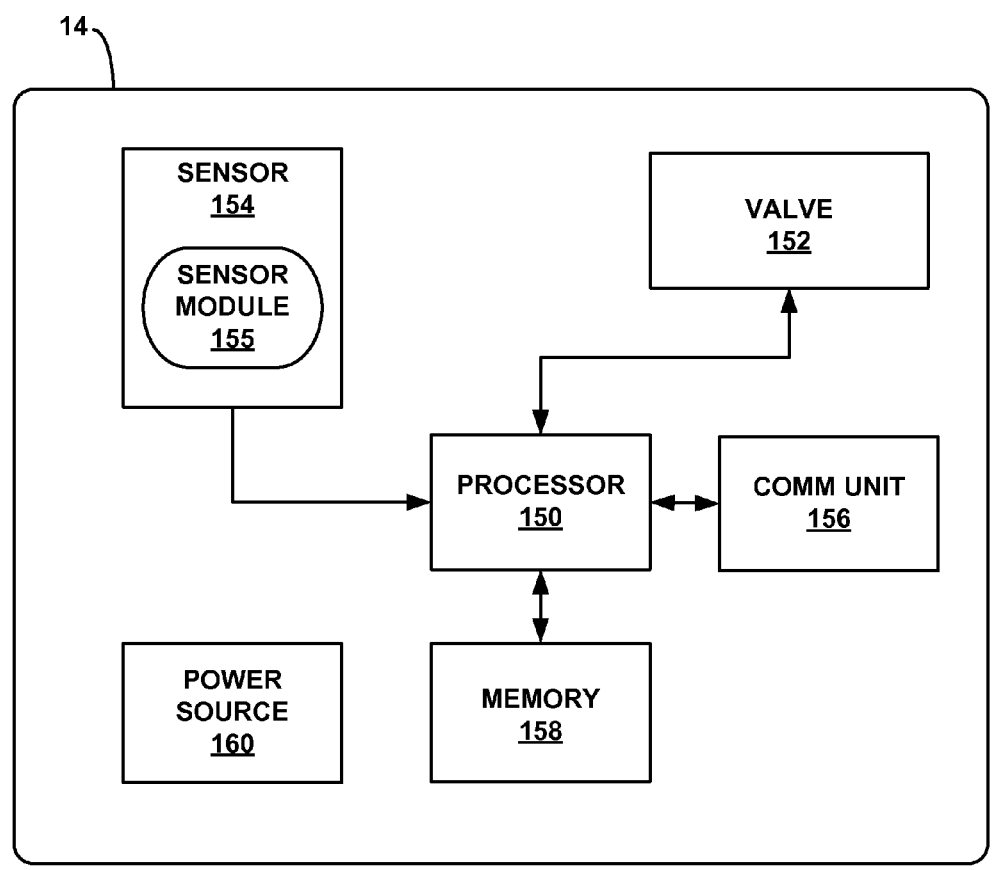
FIG. 8 is a functional block diagram illustrating an example configuration of the PMDD of FIG. 1.

FIG. 8 is a functional block diagram illustrating an example configuration of PMDD 14 of FIG. 1. In the illustrated example, PMDD 14 includes a processor 150, memory 158, valve 152, sensor 154, communication unit 156, and power source 160. Memory 158 may be a storage device that includes computer-readable instructions that, when executed by processor 150, cause PMDD 14 and processor 150 to perform various functions attributed to PMDD 14 and processor 150 herein (e.g., generating of a signal indicative of air flow and controlling valve 152). Memory 158 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 150 may include any one or more of a microprocessor, a controller, a digital signal processor (DSP), an application specific integrated circuit (ASIC), a field-programmable gate array (FPGA), or equivalent discrete or analog logic circuitry. In some examples, processor 150 may include multiple components, such as any combination of one or more microprocessors, one or more controllers, one or more DSPs, one or more ASICs, or one or more FPGAs, as well as other discrete or integrated logic circuitry. The functions attributed to processor 150 herein may be embodied as software, firmware, hardware or any combination thereof.

Processor 150 may control valve 152 to release medication to patient 13. In some examples, processor 150 may control valve 152 in response to receiving a command from computing device 22 via communication unit 156. Processor 150 may also, or alternatively, control valve 152 based in part on instructions stored in memory 158. Processor 150 may also receive a signal indicative of air flow from sensor 154 and/or a parameter value representative of the air flow. Processor 150 may store any sensed data in memory 158. Processor 150 may also store indications of valve operation, communication logs, or any other data related to the use of PMDD 14. Processor 150 may control communication unit 156 to transmit the sensor signal and/or the parameter value to computing device 22 such that computing device 22 can generate and transmit a command for valve 152 based on the sensor signal or parameter value.

Memory 158 may be configured to store a variety of operational parameters, therapy parameters, sensed and detected data, and any other information related to the monitoring, therapy and treatment of patient 12. Memory 158 may store, for example, instructions for interpreting sensor signals, instructions for controlling valve 152 based on one or more commands, volumes of air inhaled by patient 12, sub-doses and/or doses of medication delivered to patient 12, or any other operational quantitative data. In some examples, processor 150 may offload some data to computing device 22 for further analysis and/or transmission to a networked server or remote device. In some examples, memory 158 may also store communications transmitted to and/or received from LPD 16.

Sensor 154 may be any electro-magnetic sensor configured to output a signal indicative of air flow within PMDD 14. Example sensors may include rotational flow sensors, bending vane sensors, pressure sensors, or any other sensors. Sensor 154 may generate an electrical signal from mechanical deformations or movement of an element of the sensor. In some examples, sensor module 155 may calibrate the signal generated by sensor 154 to determine one or more parameter values such the velocity, flow rate, or volume of air that was delivered.

Communication unit 156 includes any suitable hardware, firmware, software or any combination thereof for communicating with another device, such as computing device 22 (FIG. 1). As described herein, communication unit 156 may transmit sensor signals or parameter values to computing device 22 and/or receive commands generated by computing device based on the sensed signal. Communication unit 156 may be configured to transfer data using any wired or wireless technique, such as Bluetooth, communication according to the 802.11 or Bluetooth specification sets, infrared communication, e.g., according to the IrDA standard, near-field communication, WiFi, or other standard or proprietary telemetry protocols.

Power source 160 may be any type of device that is configured to hold a charge to operate the circuitry of PMDD 14. Power source 160 may be provided as a rechargeable or non-rechargeable battery. In other examples, power source 160 may also incorporate an energy scavenging system that stores electrical energy from movement of PMDD 14 by patient 12.

Figure 9:
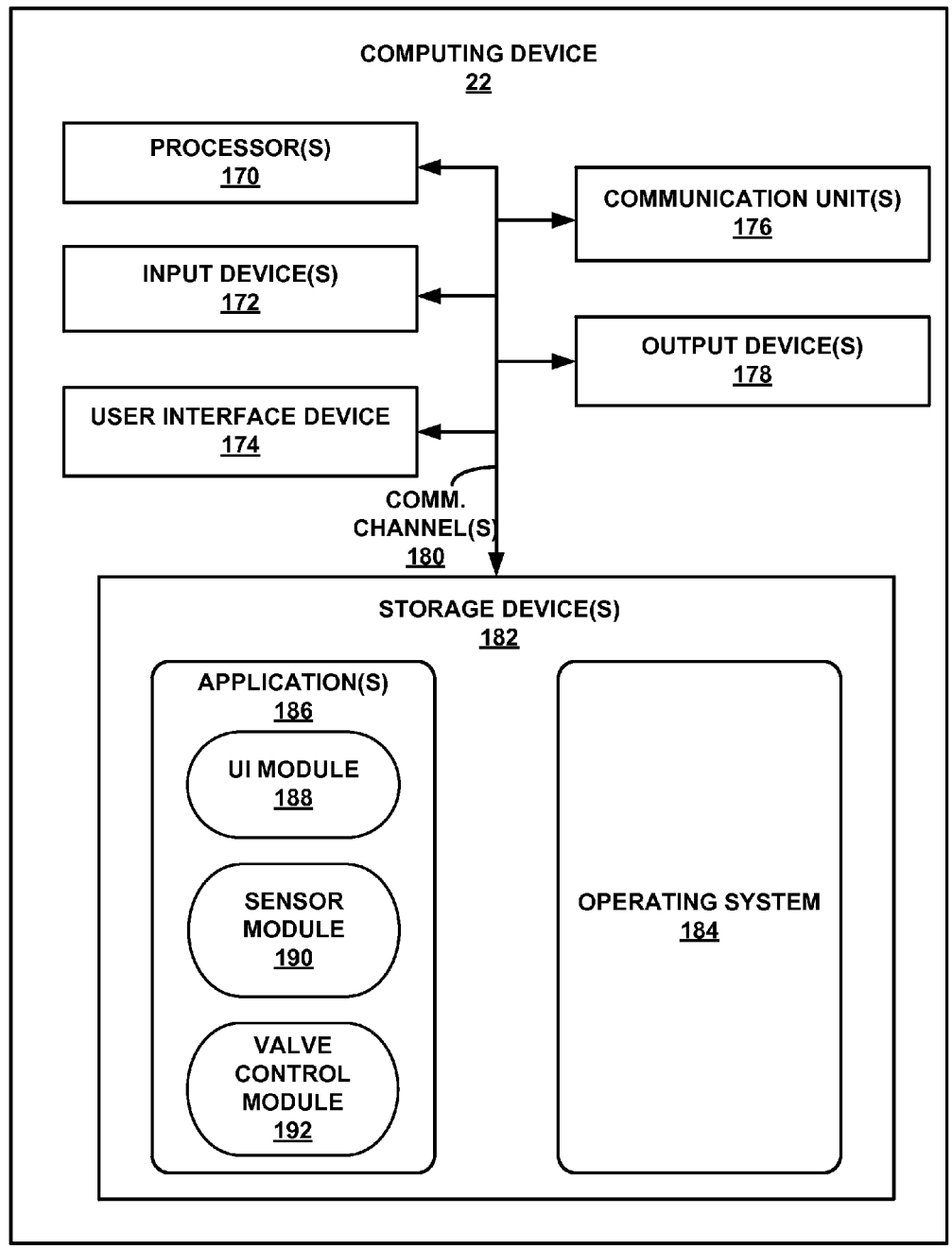
FIG. 9 is a functional block diagram illustrating an example configuration of the computing device of FIG. 1.

FIG. 9 is a functional block diagram illustrating an example configuration of the computing device 22 of FIG. 1. Computing device 22 of FIG. 9 is described below within the context of FIG. 1. In other examples, computing device 22 can include fewer, additional, or different components compared to those illustrated in FIG. 9. For example, although user interface device 174 ("UID 174") is shown in FIG. 9 as being integral with computing device 22, in other implementations, UID 1744 may be operably coupled to computing device 22, e.g., by a wired or wireless data connection. As shown in the example of FIG. 9, computing device 22 includes UID 174, one or more processors 170, one or more input devices 172, one or more communication units 176, one or more output devices 178, and one or more storage devices 182. In this example, storage devices 182 of computing device 22 also include applications 186 (including one or more of UI module 188, sensor module 190, valve control module 192) and operating system 184. Communication channels 180 may interconnect each of the components 170, 172, 174, 176, 178, 182, 186, 188, 190, 192, and 184 for inter-component communications (physically, communicatively, and/or operatively). In some examples, communication channels 180 may include a system bus, a network connection, an inter-process communication data structure, or any other method for communicating data.

One or more input devices 172 of computing device 22 may receive input. Examples of input are tactile, audio, and video input. Input devices 172 of computing device 22, in one example, includes a presence-sensitive display, touch-sensitive screen, mouse, keyboard, voice responsive system, video camera, microphone or any other type of device for detecting input from a human or machine. A presence-sensitive display may include both a presence-sensitive input device and a display device. In addition, input devices 172 may include one or more optical sensors, such as a digital camera. The one or more optical sensors may obtain images for detecting air flow within a PMDD and/or counting medication particle delivery. A microphone may also be used to detect inhalations from sound frequency and/or amplitude.

One or more output devices 178 of computing device 22 may generate output. Examples of output are tactile, audio, and video output. Output devices 178 of computing device 22, in one example, includes a presence-sensitive display (which may include a display device), sound card, video graphics adapter card, speaker, cathode ray tube (CRT) monitor, liquid crystal display (LCD), or any other type of device for generating output to a human or machine.

One or more communication units 176 of computing device 22 may communicate with external devices (e.g., a network server such as network server 254 of FIG. 12) via one or more networks (e.g., network 252 of FIG. 12) by transmitting and/or receiving network signals on the one or more networks. For example, computing device 22 may use communication unit 176 to transmit and/or receive radio signals on a radio network such as a cellular radio network. Likewise, communication units 176 may transmit and/or receive satellite signals on a satellite network such as a GPS network. Examples of communication unit 176 include a network interface card (e.g. such as an Ethernet card), an optical transceiver, a radio frequency transceiver, a GPS receiver, or any other type of device that can send and/or receive information. Other examples of communication units 176 may include Bluetooth®, GPS, 3G, 4G infrared communications, near-field communication modules, and Wi-Fi® radios found in mobile devices as well as Universal Serial Bus (USB) controllers.

UID 174 of FIG. 9 may include a presence-sensitive display. Computing device 22 may use the presence-sensitive display as an input device and an output device. For example, the presence-sensitive display of UID 174 may include a touchscreen (e.g., a presence-sensitive input device) configured to receive tactile user input from a user of computing device 22. The presence-sensitive display of UID 174 may also include a light emitting diode (LED) display (e.g., a display device) capable of outputting visible information to the user of computing device 2. UID 174 may present a user interface on the presence-sensitive display, which may be related to functionality provided by computing device 22. For example, the presence-sensitive display of UID 174 may present various functions and applications, such as an electronic message client, a map application, an Internet browser for accessing and downloading information from the Internet, and a social media application. In another example, the presence-sensitive display of UID 174 may present a menu of options related to the function and operation of computing device 22, such as screen brightness and other configurable mobile phone settings.

In some examples, the presence-sensitive display may detect an object at and/or near the screen of the presence-sensitive display. As one non-limiting example range, a presence-sensitive display may detect an object, such as a finger or stylus, which is within 2 inches or less of the physical screen of the presence-sensitive display. The presence-sensitive display may determine a location (e.g., an (x,y) coordinate) of the presence-sensitive display at or near which the object was detected. In another non-limiting example range, a presence-sensitive display may detect an object 6 inches or less from the physical screen of the presence-sensitive display, and other exemplary ranges are also possible. The presence-sensitive display may determine the location selected by the object (e.g., user's finger) using capacitive, inductive, and/or optical recognition techniques. In some examples, the presence-sensitive display provides output using tactile, audio, or video stimuli as described with respect to output device 178.

One or more storage devices 182 within computing device 22 may store information required for use during operation of computing device 22. Storage devices 182, in some examples, have the primary purpose of being short term and not long-term computer-readable storage mediums. Storage devices 182 on computing device 22 may be configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art. Storage devices 182 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage devices 182 may store program instructions, data obtained from a PMDD or generated based on PMDD signals, and/or data associated with applications 186, UI module 188, sensor module 190, valve control module 192, and operating system 52.

One or more processors 170 may implement functionality and/or execute instructions within computing device 22. For example, processors 170 on computing device 22 may read and execute instructions stored by storage devices 182 that execute the functionality of applications 186, UI module 188, sensor module 190, and valve control module 192. These instructions executed by processors 170 may cause computing device 22 to store information within storage devices 182 during program execution, such as notifications, notification objects, and/or information associated applications 186 or any of modules 188, 190, and 192. Processors 170 may execute instructions of applications 186 and/or modules 188, 190, and 192 to perform various functions related to the delivery of medication from a PMDD. For examples, UI module 188 may generate for output visual information related to applications 188. Sensor module 190 may be configured to generate parameter values representative of air flow from received or detected sensor signals. In addition, valve control module 192 may be configured to generate commands that cause a valve of PMDD to open or close. In other examples, one or more processors 170 may execute instructions of any of applications 186 or modules 188, 190, and 192 to request a network server to perform (or at least partially perform) any of the functions attributed to modules 188, 190, and 192 herein.

Although the components of computing device 22 are illustrated in the example of FIG. 9 as within a common housing, one or more components may instead be wired or wirelessly tethered to computing device 22. For example, output device 178 (e.g., a display device) may be physically separate from computing device 22. In other examples, an optical sensor may not reside within a housing of computing device 22.

Computing device 22 may also store data related to the use of PMDD 14 in storage devices 182. For example, computing device 22 may store information or data related to the use of PMDD 14. For example, stored data may include information indicating the time each dose and/or sub-dose of medication was delivered, the frequency with which medication was delivered, the amount of medication delivered to the patient, the amount of medication remaining in a canister, the number of prescription refills remaining in an account of patient 12, changes in frequency with which patient 12 requests medication, or any other information related to the use of PMDD 14 and/or computing device 22. Computing device 22 may transmit this information to a clinician device (e.g., remote device 258 of FIG. 12) or a sever (networked server 254 of FIG. 12) periodically, in response to generation of the data, and/or in response to a request for the information.

In other examples, the combination of PMDD 14 and computing device 22 may function as a spirometer or any other system configured to obtain information regarding the function of the patient's lungs. For example, computing device 22 may receive signals or parameter values indicative of air flow speed, flow rate, pressure, and/or volume during patient inhalation and/or exhalation. Computing device 22 may receive this data during medication delivery via PMDD 14 or during a separate session in which patient 12 uses PMDD 14 for diagnostic purposes. Computing device 22 may collect the data related to air flow within PMDD 14 and store the data for later use. For example, computing device 22 may generate one or more lung parameter values (e.g., total lung volume, tidal volume, etc.). Computing device 22 may output for display representation of this lung related data to patient 12 and/or a clinician. In some examples, computing device 22 may transmit this information to a remote device via a network periodically or in response to a request received over the network. Using the network capabilities of computing device 22, a clinician may review lung information from computing device 22 to diagnose patient 12 without an in-person appointment. In other locations, computing device 22 may analyze the lung information and transmit a notification and/or the lung information in response to detecting a parameter value indicative of a change in patient condition and/or exceeding a predetermined threshold.

Computing device 22 may also use a microphone to monitor the breathing status of patient 12. As described herein, the microphone may be used to generate data indicative of an inhalation. In addition, computing device 22 may store sounds acquired by the microphone to track the frequency of breaths, the duration of each breath, indications of breathing difficulties, or any other parameters related to breathing. This data related to breathing sounds may be stored in storage devices 182 and/or transmitted to a remote device for review by a clinician. The clinician may monitor this data to identify ineffective medication and/or send a message to patient 12 requesting to set up a follow-up appointment.

In some examples, application 186 for controlling PMDD 14 may monitor the power source of computing device 22 to ensure that there is enough power for emergency use. For example, application 186 may cause processor 170 to maintain a reserve of power for emergency purposes. When the power level (e.g., voltage) of computing device 22 drops below a predetermined threshold (e.g., approximately between 5% and 15%), application 186 may cause processor 170 to shut down. This premature shutdown may preserve some emergency battery power for future medication delivery from PMDD 14 and/or alternative uses of computing device 22 (e.g., emergency phone calls). Application 186 may output the power or time remaining before this shut down will begin. Alternatively, application 186 may prompt the user to shut down computing device 22, but application 186 will not automatically shut down the device.

Figure 10:
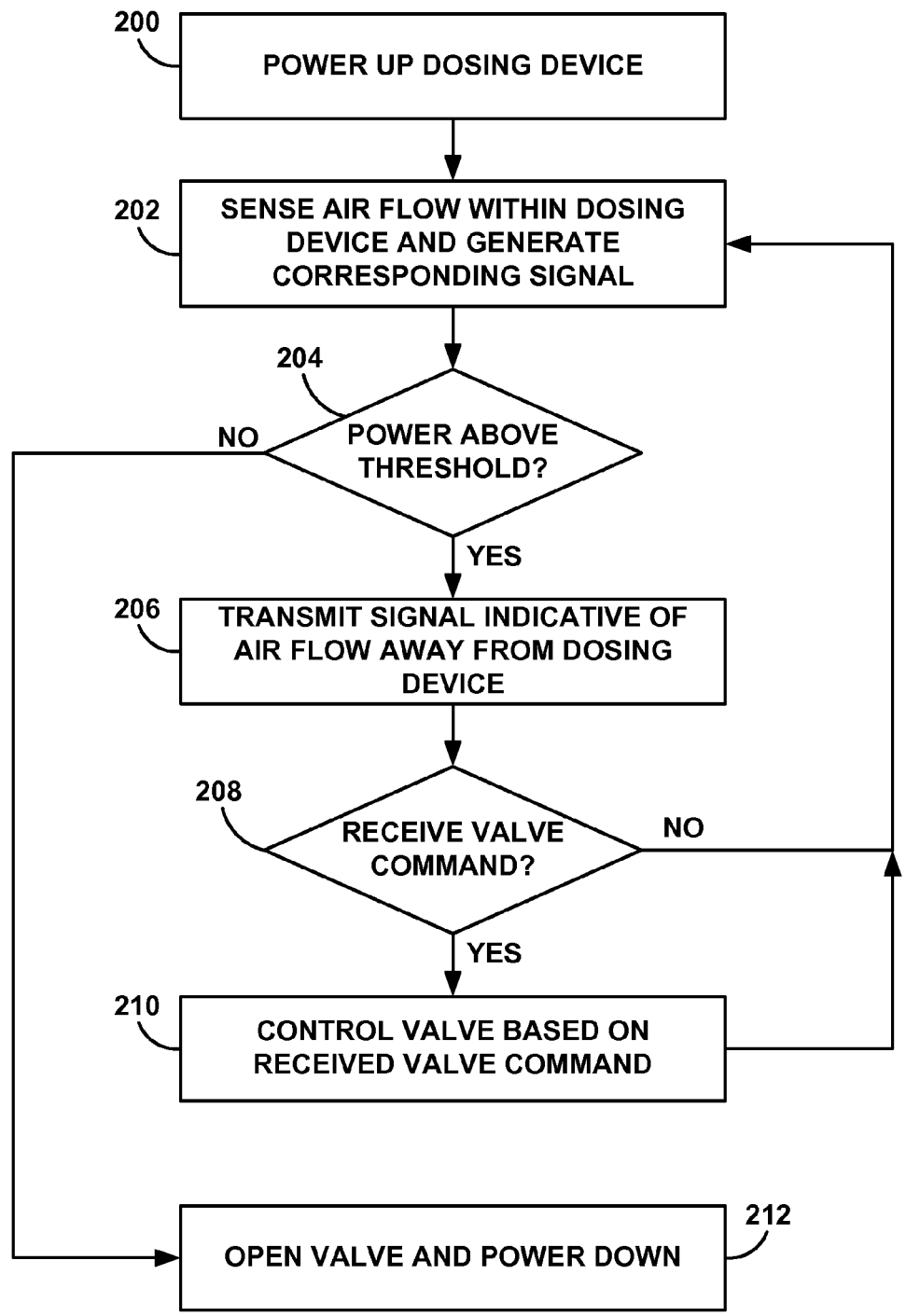
FIG. 10 is a flow diagram of an example process for controlling delivery of medication from a PMDD.

FIG. 10 is a flow diagram of an example process for controlling delivery of medication from a PMDD. The example processor of FIG. 10 is described with respect to components (e.g., processor 150, sensor 154, and valve 152) of PMDD 14 of FIGS. 1 and 8. However, any of PMDDs 14, 26, 33, 50, 80, and 140 may perform the process of FIG. 10 in other examples. In some examples, one or more steps of the process of FIG. 10 may be performed by a different computing device (e.g., computing device 22), and PMDD 14 may also perform one or more functions attributed to computing device 22.

As shown in FIG. 10, PMDD 14 may power up, or turn on, in response to receiving a user input requesting that PMDD 14 is turned on (200). Alternatively, PMDD 14 may power up from a reduced power state in response to time schedule to power up and/or a sensor indicating that patient 12 may desire to use PMDD 14 (e.g., an accelerometer detecting an acceleration that patient 12 has picked up PMDD 14. Once powered up, processor 150 may control sensor 154 to sense the air flow within PMDD 14 and generate a signal indicative of the sensed air flow to be transferred to processor 150 (202). In some examples, sensing air flow may include sensing a velocity of air flow using a flow sensor. In other examples, air flow may be sensed using one or more pressure sensors, where changes in pressure are indicative of magnitude and/or direction of air flow within PMDD 14. In some examples, sensor module 155 may also determine one or more parameter values (e.g., a flow velocity, a flow rate, pressure, etc.) representing the signal.

Processor 150 may also determine if the power (e.g., voltage) of power source 160 is above a threshold sufficient to maintain operation of PMDD 14 and delivery of medication to patient 12 (204). If processor 150 determines that the power is not above a threshold ("NO" branch of block 204), processor 150 may control valve 152 to be opened and control PMDD 14 to power down (212). In addition, processor 150 may open valve 152 and power down PMDD 14 in response to detection of a malfunction in PMDD 14 or computing device 22 that would prevent delivery of medication. Although this determination step is described before the transmission step 206, processor 150 may perform this check at any point in the process or even in parallel with other functions. This step may be provided to allow manual use of PMDD 14 in circumstances in which valve 152 may be prevented from proper function. In other examples, computing device 22 may transmit a command to open valve 152 when the power supply of computing device 22 is below a threshold, such as 10-15% remaining power.

If processor 150 determines that the power of power source 160 is above the threshold ("YES" branch of block 204), processor 150 may control communication unit 156 to transmit the signal indicative of air flow to computing device 22 (206). The signal may thus be indicative of inhalation, and computing device may generate an appropriate command for valve 152. If processor 150 does not receive any valve command ("NO" branch of block 208), processor 150 may instruct sensor 154 to continue generating signals indicative of the air flow (e.g., pressure and/or flow signals indicative of moving air) (202). If processor 150 does receive a valve command from computing device 22 via communication unit 156 ("YES" branch of block 208), processor 150 controls valve 152 based on the valve command (210). For example, processor 150 may control the valve to open and release medication to patient 12 or close when the dose or sub-dose has been delivered. In this manner, processor 150 may control the value to release any sized dose (e.g., a partial dose or full dose of medication) to patient 12 in a single continuous release of medication. Processor 150 may subsequently instruct sensor 154 to continue generating signals indicative of the air flow (202).

In other examples, processor 150 may control valve 152 without the use of computing device 22. For example, processor 150 may be configured to receive the signal from sensor 154, determine one or more parameter values based on the signal, generate a command for valve 152 based on the parameter values, and control valve 152 to open or close based on the command. In this manner, PMDD 14 may be configured to deliver medication to patient 12 independently (e.g., without communications to or from another device). In some examples, these functions may be performed by multiple processors and/or modules executed by one or more processors.

Figure 11:
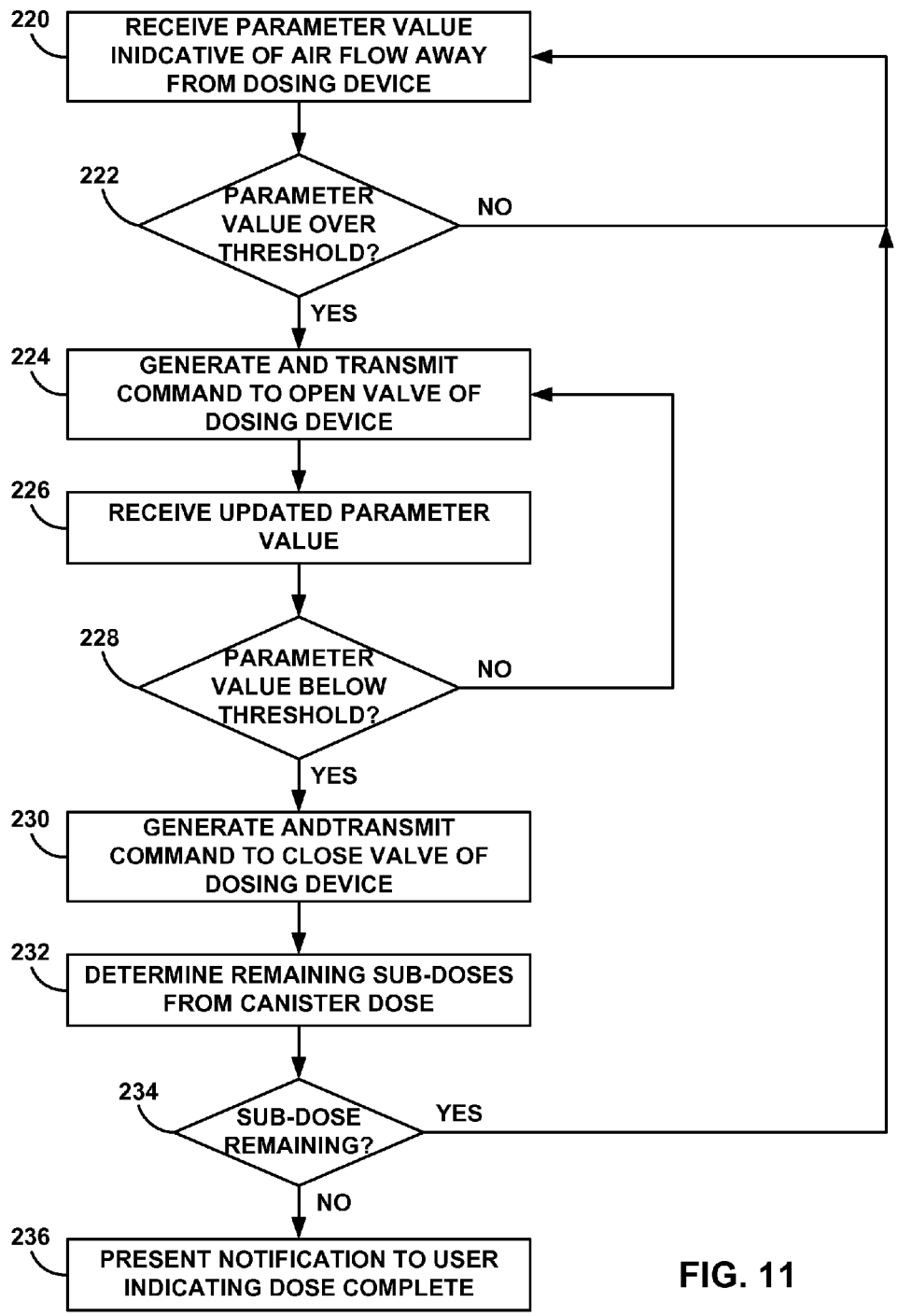
FIG. 11 is a flow diagram of an example process for delivering sub-doses of medication from a PMDD based on detected air flow within the PMDD.

FIG. 11 is a flow diagram of an example process for delivering sub-doses of medication from a PMDD based on detected air flow within the PMDD. The example processor of FIG. 11 is described with respect to components (e.g., processor 170, UI device 174, and communication unit 176) of computing device 22 of FIGS. 1 and 9. However, in other examples, one or more aspects of the processor of FIG. 11 may be performed by one of PMDDs 14, 26, 33, 50, 80, and 140 instead of at the different device of computing device 22.

As shown in FIG. 11, processor 170 may receive a parameter valve from PMDD 14 indicative of air flow away from PMDD 14, such as an inhalation of patient 12 (220). In other examples, processor 170 may receive data indicative of a sensor signal, and processor 170 may first determine the parameter valve from the received signal. For example, sensor module 190 of application 186 may determine the parameter values. The parameter value may represent whether or not patient 12 is inhaling. If processor 170 determines that the parameter value is below a threshold ("NO" branch of block 222), processor 170 may continue to receive parameter values (220). If processor 170 determines that the parameter value is above or over the threshold ("YES" branch of block 222), processor 170 generates a command for the valve of PMDD 14 and controls communication unit 176 to transmit the command to PMDD 14 (224). Processor 170 may execute valve control module 192, for example, to generate the commands for the valve of PMDD 14.

Processor 170 may subsequently receive an updated parameter value from PMDD 14 (226). If processor 170 determines that the parameter value is still above the threshold ("NO" branch of block 228), processor 170 may generate and transmit the command to keep the valve open to dispense the medication to the patient (224). If processor 170 determines that the parameter value is below the threshold ("YES" branch of block 228), processor 170 may generate a command to close the valve of PMDD 14 and control communication unit 176 to transmit the command to PMDD 14 (230). This single cycle of opening and closing the valve of PMDD 14 may have caused a sub-dose of medication to be delivered to patient 12 during a single inhalation.

Processor 170 may determine if there are any remaining sub-doses to be delivered (232). Processor 170 may use information such as the amount of medication in a full dose, the rate of delivery of medication when the valve is open, the duration of which the valve was open, and the speed or flow rate of air flow sensed during the inhalation, to determine a volume of inhaled air and/or amount of medication delivered to patient 12. Processor 170 may then determine if any amount of medication remains to be delivered from the full dose of medication. If processor 170 determines that there is at least one sub-dose remaining ("YES" branch of block 234), processor 170 may continue to receive parameter values from PMDD 14 (220). If processor 170 determines that there are no more sub-doses remaining ("NO" branch of block 234), processor 170 may instruct UI module 188 to output, for presentation at UI device 174, a notification to the user or patient 12 indicating that the full dose is complete and has been delivered (236). The notification may be a visual notification, an audible notification, a haptic notification (e.g., a vibration), or any combination thereof.

FIG. 12 is a conceptual diagram of an example system 240 that includes a computing device 242 and a networked server 254 associated with use of PMDD 14. Although computing device 242 may determine parameter values, compare parameter values to thresholds, and generate valve commands to control the release of medication from a PMDD (e.g., PMDD 14), computing device 242 may offload one or more processing tasks to a networked server 254. Networked server 254 may provide additional processing power and/or access to updated clinical instructions related to the use of PMDD 14. In addition, data obtained by computing device 242 may be transmitted for storage at repository 256 and/or remote device 258. Using remote device 258, a clinician may track the use of a PMDD and the condition of patient 12.

As shown in FIG. 12, system 240 includes computing device 242 (e.g., an example of computing device 22 of FIGS. 1 and 9), network 252, networked server 254, and repository 256. Computing device 242, in some examples, is or is a part of a portable computing device (e.g., a mobile phone, a smartphone, a netbook, a notebook, a tablet device, or a smart watch). In other examples, computing device 242 may be at least a part of a digital camera, a music player, or any other device that a user may carry or move between different locations. Computing device 242 may also connect to network 252 (e.g., a wired or wireless network). Although network 252 may be a single network, network 252 may be representative of two or more networks that allow computing device 242 to communicate with networked server 252.

Computing device 242 may include display device 244, rear camera 250 (e.g., an optical sensor), microphone 246, and speaker 248. Display device 244 may include one or more input devices and/or output devices so that the user can communicate with computing device 242. In one example, display device 244 may include a touch screen interface (e.g., a presence-sensitive display that includes a presence-sensitive input device). In other examples, display device 244 may include a display and one or more buttons, pads, joysticks, mice, tactile device, or any other device capable of turning user actions into electrical signals that control computing device 242. In any example, the user may interact with display device 154 or any other input devices to provide input prior to or during the processes described herein.

Rear camera 250 may enable computing device 242 to capture images (e.g., still images and/or video) of the environment surrounding computing device 242, including detection of a moving element of a PMDD. Rear camera 250 may include one or more optical sensors capable of generating high-resolution images. For example, the optical sensor may include more than one million pixels (a one megapixel sensor), more than five million pixels (a five megapixel sensor), or even more than ten million pixels (a ten megapixel sensor). In some examples, computing device 242 may include two or more cameras disposed on any surface of computing device 242 or coupled to computing device 242 using a cable. Alternatively, rear camera 250 may be placed on the front or other surface of computing device 242.

Microphone 246 may be configured to capture sound around computing device 242, such as user speech, speech from other people, and environmental sounds including inhalations from patient 12. Speaker 248 may be configured to generate and deliver audio to the user such as contact speech or other sounds. In some examples, computing device 242 may include more than one microphone 246 and speaker 248. Although microphone 246 and speaker 248 may be located on or within a housing of computing device 242, microphone 246 and/or speaker 248 may be electrically coupled to computing device 242 via one or more cables. Microphone 246 is an example of an audio input and speaker 248 is an example of an audio output. In other examples, computing device 242 may include additional, or alternative, audio inputs and audio outputs that include a sensor or direct electrical connection configured to accept audio from an attached device or deliver audio to an attached device.

Computing device 242 and networked server 254 may cooperatively function to provide the functionality described herein. Computing device 242 may determine the geographical location at which the computing device is located. For example, computing device 242 may include a device location module, for example, that obtains data from GPS satellites, cellular network access points, or local area network access points, or any other device from which data regarding the position of computing device 242 can be obtained. Computing device 242 and/or networked server 254 may use this geographical location of computing device 242 to suggest when to take a dose of medication based on reported air quality readings, excessive heat, excessive cold, known circumstances certain cities or rural areas, or even air particulates such as pollen or other allergens. These environmental indications may be obtained from a manufacturer of the PMDD, the medication, another company, a clinic or hospital, or a governmental agency. Computing device 242 may then provide an alert to patient 12 to suggest steps to avoid such areas, take a dose of medication to prevent possible symptoms, or otherwise modify medication dosage or therapy.

Transmission of information or any other data from computing device 242, may require a connection between computing device 242 and networked server 254 using network 252. Both computing device 242 and network server 254 may connect to network 252. Network 252 may be embodied as one or more of the Internet, a wireless network, a wired network, a cellular network, or a fiber optic network. In other words, network 252 may be any data communication protocol or protocols that facilitate data transfer between two or more devices. Network server 254 may also connect to repository 256 for storing sets of data or retrieving archived data related to patient 12 or the use of PMDD 14. Network server 254 and repository 256 may each include one or more servers or databases, respectively. Network server 254 may include one or more servers, desktop computers, mainframes, minicomputers, or other computing devices capable of executing computer instructions and storing data. In some examples, functions attributable to computing device 242 or computing device 22 herein may be attributed to respective different servers such as networked server 254 for respective functions. Repository 256 may include one or more memories, repositories, hard disks, or any other data storage device. In some examples, repository 256 may be included within network server 254.

Repository 256 may be included in, or described as, cloud storage. Network server 254 may access the cloud and retrieve data as necessary. In some examples, repository 256 may include Relational Database Management System (RDBMS) software. In one example, repository 256 may be a relational database and accessed using a Structured Query Language (SQL) interface that is well known in the art. Repository 256 may alternatively be stored on a separate networked computing device and accessed by network server 254 through a network interface or system bus. Repository 256 may in other examples be an Object Database Management System (ODBMS), Online Analytical Processing (OLAP) database or other suitable data management system.

The following examples illustrate example methods, devices, and systems described herein. Example 1: a method comprising generating a signal indicative of air flow within a portion of a pulmonary medication dosing device, receiving, by a processor, a command based on the signal and associated with a valve configured to at least partially control release of a medication via the pulmonary medication dosing device, and controlling, by the processor and based on the received command, the valve to release at least a portion of a dose of the medication into the air flow.

Example 2: the method of example 1, wherein the dose of the medication is a full dose of the medication released by a medication canister coupled to the pulmonary medication dosing device and retained within a dosing chamber prior to generation of the signal, and wherein the portion of the full dose is a sub-dose of the medication.

Example 3: the method of any of examples 1 and 2, wherein receiving the command comprises receiving a first command indicating opening of the valve, and wherein the method further comprises receiving a second command indicating closing of the valve and controlling, based on the received second command, the valve to close.

Example 4: the method of any of examples 1 to 3, further comprising determining, based on the signal, a parameter value representative of the signal indicative of the air flow.

Example 5: the method of example 4, wherein the parameter value is indicative of at least one of a flow rate, a velocity, or pressure of the air flow through the portion of the pulmonary medication dosing device.

Example 6: the method of any of examples 1 to 5, wherein generating the signal comprises generating, by a sensor, an electrical signal indicative of the air flow within the portion of the pulmonary medication dosing device.

Example 7: the method of any of examples 1 to 6, wherein generating the signal comprises producing a detectable visual indication of the air flow within the portion of the pulmonary medication dosing device.

Example 8: the method of any of examples 1 to 7, wherein receiving the command comprises receiving the command from a communication unit of a computing device different from the pulmonary medication dosing device.

Example 9: the method of example 8, further comprising, responsive to generating the signal, transmitting the generated signal to the computing device.

Example 10: the method of example 9, wherein the pulmonary medication dosing device comprises the processor, and wherein the method further comprises receiving, by the computing device, the generated signal from a communication unit of the pulmonary medication dosing device, responsive to receiving the generated signal, generating, by the computing device and based on the signal indicative of air flow within the portion of the pulmonary medication dosing device, the command, and transmitting, by the communication unit of the computing device, the generated command to the processor.

Example 11: the method of example 8, wherein the computing device comprises a mobile computing device.

Example 12: the method of any of examples 1 to 11, wherein the pulmonary medication dosing device comprises a removably coupled mouthpiece defining at least one intake opening and comprising the valve and a dosing chamber, the dosing chamber attached to the valve and an orifice of the pulmonary medication dosing device through which medication is dispensed.

Example 13: the method of any of examples 1 to 12, wherein controlling the valve to release at least the portion of the dose of medication into the air flow comprises controlling the valve to release the dose of medication into the air flow.

Example 14: the method of any of examples 1 to 13, wherein the pulmonary medication dosing device comprises the processor.

Example 15: a pulmonary medication dosing device, the device comprising a valve configured to at least partially control release of medication, a sensor configured to generate a signal indicative of air flow within a portion of the device, and a processor configured to receive a command based on the signal and associated with the valve and control, based on the received command, the valve to release at least a portion of a dose of the medication into the air flow.

Example 16: the device of example 15, wherein the portion of the dose of the medication is a sub-dose of a full dose of the medication, and wherein the device further comprises a dosing chamber coupled to the valve and configured to retain the full dose of the medication released by a medication canister coupled to the device prior to generation of the signal.

Example 17: the device of any of examples 15 and 16, wherein the command is a first command indicating opening of the valve, and wherein the processor is configured to receive a second command indicating closing of the valve and controlling, based on the received second command, the valve to close.

Example 18: the device of any of examples 15 to 17, further comprising a sensor module configured to determine, based on the signal, a parameter value representative of the signal indicative of the air flow.

Example 19: the device of example 18, wherein the parameter value is indicative of at least one of a flow rate, a velocity, or a pressure of the air flow through the portion of the pulmonary medication dosing device.

Example 20: the device of any of examples 15 to 19, wherein the sensor is configured to generate an electrical signal indicative of the air flow within the portion of the pulmonary medication dosing device.

Example 21: the device of any of examples 15 to 20, wherein the sensor comprises an element configured to move within and as a function of the air flow, and wherein movement of the element produces a detectable visual indication of the air flow within the portion of the pulmonary medication dosing device.

Example 22: the device of any of examples 15 to 21, wherein the processor is configured to receive the command from a communication unit of a computing device different from the pulmonary medication dosing device.

Example 23: the device of example 22, further comprising a communication unit of the pulmonary medication dosing device configured to, responsive to generating the signal, transmit the generated signal to the computing device.

Example 24: the device of any of examples 15 to 23, further comprising a mouthpiece removably coupled to a housing of the pulmonary medication dosing device, wherein the mouthpiece comprises the portion of the pulmonary medication dosing device, defines at least one intake opening through which at least a portion of the air flow originates, and comprises the valve and a dosing chamber, the dosing chamber attached to the valve and an orifice of the housing through which medication is dispensed.

Example 25: the device of any of examples 15 to 24, wherein the valve is configured to release at least the portion of the medication from a medication canister while a metering valve of the medication canister is in an open configuration.

Example 26: the device of any of examples 15 to 25, wherein at least the portion of the dose of the medication comprises a full dose of the dose of the medication.

Example 27: a system comprising a housing configured to accept a medication canister containing a medication, a dispensing portion coupled to the housing, a valve configured to at least partially control release of medication from the medication canister, a sensor configured to generate a signal indicative of air flow within the dispensing portion, and a processor configured to receive a command based on the signal and associated with the valve and control, based on the received command, the valve to release at least a portion of a dose of the medication into the air flow within the dispensing portion.

Example 28: the system of example 27, wherein the dispensing portion comprises a mouthpiece configured to be placed within a mouth of a user during release of at least the portion of the dose of the medication.

Example 29: the system of any of examples 27 and 28, wherein the dispensing portion comprises a connector configured to couple the device to breathing circuit tubing.

Example 30: the system of any of examples 27 to 29, further comprising a communication unit configured to transmit the generated signal to a computing device different than the processor and receive, from the computing device, the command.

Example 31: the system of any of examples 27 to 30, wherein the processor is configured to generate, based on the signal, the command.

Example 32: the system of any of examples 27 to 31, wherein at least the portion of the dose of the medication comprises a full dose of the dose of the medication.

Example 33: a computer-readable storage medium comprising instructions that, when executed by one or more processors of a computing device, cause the one or more processors to receive data indicative of air flow within a portion of a pulmonary medication dosing device, responsive to receiving the data, generate, based on the received data, a command associated with a valve configured to at least partially control release of a medication via the pulmonary medication dosing device, and wherein the command indicates one of an open configuration or a closed configuration of the valve, and transmit the command to a communication unit associated with the pulmonary medication dosing device.

The disclosure also contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to any of PMDD 14, 26, 33, 50, 80, and 140, computing device 22, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between PMDD 14 and computing device 22, for example. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described for delivering pulmonary medication to a patient in response to detecting inhalations. Any combination of the described operations, functions, or devices is included.

What is claimed is:

1. A pulmonary medication dosing device, the device comprising:
   a dosing chamber configured to retain a single full dose of a medication released by a metering valve of a medication canister coupled to the device upon the medication canister being depressed a single time;
   a controllable valve coupled to the dosing chamber and configured to at least partially control release of respective sub-doses of the single full dose of the medication for different inhalation events;
   a sensor configured to generate a signal indicative of air flow within a portion of the device, the air flow associated with the different inhalation events; and
   a processor configured to:
      receive a command generated from the signal and associated with the controllable valve; and
      control, based on the received command, the controllable valve to release the respective sub-doses of the medication into the air flow of the different air flow events until the single full dose has been released by the controllable valve.

2. The device of claim 1, wherein the full dose of the medication is released by the metering valve of the medication canister to the dosing chamber prior to generation of the signal.

3. The device of claim 1, wherein the command is a first command indicating opening of the controllable valve, and wherein the processor is configured to:
   receive a second command indicating closing of the controllable valve; and
   controlling, based on the received second command, the controllable valve to close.

4. The device of claim 1, further comprising a sensor module configured to determine, based on the signal, a parameter value representative of the signal indicative of the air flow.

5. The device of claim 4, wherein the parameter value is indicative of at least one of a flow rate, a velocity, or a pressure of the air flow through the portion of the pulmonary medication dosing device.

6. The device of claim 1, wherein the sensor is configured to generate an electrical signal indicative of the air flow within the portion of the pulmonary medication dosing device.

7. The device of claim 1, wherein the sensor comprises an element configured to move within and as a function of the air flow, and wherein movement of the element produces a detectable visual indication of the air flow within the portion of the pulmonary medication dosing device.

8. The device of claim 1, wherein the processor is configured to receive the command from a communication unit of a computing device different from the pulmonary medication dosing device.

9. The device of claim 8, further comprising a communication unit of the pulmonary medication dosing device configured to, responsive to generating the signal, transmit the generated signal to the computing device.

10. The device of claim 8, wherein the computing device comprises a mobile computing device.

11. The device of claim 1, wherein the processor is configured to generate, based on the signal indicative of air flow within the portion of the device, the command.

12. The device of claim 1, further comprising a mouthpiece removably coupled to a housing of the pulmonary medication dosing device, wherein the mouthpiece:
   comprises the portion of the pulmonary medication dosing device;
   defines at least one intake opening through which at least a portion of the air flow originates; and
   comprises the controllable valve and the dosing chamber, the dosing chamber attached to the controllable valve and an orifice of the housing through which medication is dispensed.

13. The device of claim 1, wherein the processor is configured to:

determine that no more sub-doses of the single full dose of medication remain to be delivered from the dosing chamber; and responsive to determining that no more sub-doses remain, instruct a user interface module to output a notification to a user indicating that the single full dose has been delivered.

14. The device of claim 1, wherein the processor is configured to set the controllable valve to an open configuration after the single full dose of medication is released from the dosing chamber by the controllable valve.

15. A method comprising:
generating, by a sensor, a signal indicative of air flow within a portion of a pulmonary medication dosing device, the air flow associated with different inhalation events, wherein:
   a dosing chamber is configured to retain a single full dose of a medication released by a metering valve of a medication canister coupled to the pulmonary medication dosing device upon the medication canister being depressed a single time; and
   a controllable valve is coupled to the dosing chamber and configured to at least partially control release of respective sub-doses of the single full dose of the medication for the different inhalation events;
receiving, by a processor, a command generated from the signal and associated with the controllable valve; and
controlling, by the processor and based on the received command, the controllable valve to release the respective sub-doses of the medication into the air flow of the different air flow events until the single full dose has been released by the controllable valve.

16. The method of claim 15, wherein the full dose is retained within the dosing chamber prior to generation of the signal.

17. The method of claim 15, wherein receiving the command comprises receiving a first command indicating opening of the controllable valve, and wherein the method further comprises receiving a second command indicating closing of the controllable valve and controlling, based on the received second command, the controllable valve to close.

18. The method of claim 15, further comprising determining, based on the signal, a parameter value representative of the signal indicative of the air flow, wherein the parameter value is indicative of at least one of a flow rate, a velocity, or pressure of the air flow through the portion of the pulmonary medication dosing device.

19. The method of claim 15, wherein receiving the command comprises receiving the command from a communication unit of a mobile computing device different from the pulmonary medication dosing device, and wherein the method further comprises, responsive to generating the signal, transmitting the generated signal to the computing device.

20. A system comprising:
means for generating a signal indicative of air flow within a portion of a pulmonary medication dosing device, the air flow associated with different inhalation events, wherein:
   a dosing chamber is configured to retain a single full dose of a medication released by a metering valve of a medication canister coupled to the pulmonary medication dosing device upon the medication canister being depressed a single time; and
   a controllable valve is coupled to the dosing chamber and configured to at least partially control release of respective sub-doses of the single full dose of the medication for the different inhalation events;
means for receiving a command generated from the signal and associated with the controllable valve; and
means for controlling, based on the received command, the controllable valve to release the respective sub-doses of the medication into the air flow of the different air flow events until the single full dose has been released by the controllable valve.

* * * * *